United States Patent
Akao et al.

(10) Patent No.: US 11,450,901 B2
(45) Date of Patent: Sep. 20, 2022

(54) POWER SUPPLY UNIT FOR AEROSOL INHALER, AND CONTROL METHOD AND CONTROL PROGRAM OF THE SAME

(71) Applicant: Japan Tobacco Inc., Tokyo (JP)

(72) Inventors: Takeshi Akao, Tokyo (JP); Manabu Yamada, Tokyo (JP); Hajime Fujita, Tokyo (JP)

(73) Assignee: JAPAN TOBACCO INC., Tokyo (JP)

(*) Notice: Subject to any disclaimer, the term of this patent is extended or adjusted under 35 U.S.C. 154(b) by 0 days.

(21) Appl. No.: 16/726,944

(22) Filed: Dec. 26, 2019

(65) Prior Publication Data

US 2020/0212517 A1    Jul. 2, 2020

(30) Foreign Application Priority Data

Dec. 27, 2018  (JP) .............................. JP2018-244967

(51) Int. Cl.
  *H01M 10/48*  (2006.01)
  *H02H 7/20*  (2006.01)
  *A61M 15/06*  (2006.01)

(52) U.S. Cl.
  CPC .......... *H01M 10/488* (2013.01); *A61M 15/06* (2013.01); *H02H 7/20* (2013.01)

(58) Field of Classification Search
  CPC ...... H01M 10/488; H01M 10/48; H02H 7/20; A61M 15/06; A24F 40/53; A24F 40/90; A24F 40/51; A24F 40/10; G01R 31/382; G01R 31/3646; G01R 31/52
  USPC ....................................................... 320/134
  See application file for complete search history.

(56) References Cited

U.S. PATENT DOCUMENTS

| | | | | |
|---|---|---|---|---|
| 6,255,803 B1* | 7/2001 | Ishihara | ............. | G01R 31/3835 320/134 |
| 6,358,058 B1* | 3/2002 | Strupat | ................ | A61B 5/0876 434/262 |
| 8,120,325 B2* | 2/2012 | Wolf | ....................... | G01R 31/36 320/136 |
| 2003/0000524 A1* | 1/2003 | Anderson | ......... | A61M 15/0068 128/203.23 |
| 2003/0052646 A1* | 3/2003 | Minamiura | ............... | B60L 3/12 320/122 |

(Continued)

FOREIGN PATENT DOCUMENTS

| CN | 101425678 A | 5/2009 |
|---|---|---|
| CN | 203446536 U | 2/2014 |

(Continued)

OTHER PUBLICATIONS

Notification of Reasons for Refusal received for Japanese Patent Application No. 2018-244967, dated May 14, 2019, 6 pages including English Translation.

(Continued)

*Primary Examiner* — Richard Isla
*Assistant Examiner* — Dung V Bui
(74) *Attorney, Agent, or Firm* — Xsensus LLP

(57) ABSTRACT

A power supply unit for an aerosol inhaler includes: a power supply able to discharge power to a load for generating an aerosol from an aerosol source; a control unit configured to control the power supply; and a sensor configured to output a value related to a remaining amount of the power supply. The control unit detects a short circuit of the power supply based on an output value of the sensor.

20 Claims, 16 Drawing Sheets

(56) References Cited

U.S. PATENT DOCUMENTS

| | | | |
|---|---|---|---|
| 2004/0257042 A1* | 12/2004 | Liu | H02J 7/0018 320/130 |
| 2006/0220626 A1* | 10/2006 | Partridge | H02M 7/48 323/282 |
| 2007/0062523 A1* | 3/2007 | Sexton | A61M 15/009 128/200.24 |
| 2009/0108808 A1 | 4/2009 | He et al. | |
| 2010/0188050 A1* | 7/2010 | Asakura | H01M 10/4235 320/136 |
| 2010/0194398 A1 | 8/2010 | Kawasumi et al. | |
| 2014/0254055 A1 | 9/2014 | Xiang et al. | |
| 2014/0258741 A1* | 9/2014 | Xiang | G06F 1/26 713/300 |
| 2014/0345635 A1* | 11/2014 | Rabinowitz | A24B 15/16 131/352 |
| 2015/0090277 A1* | 4/2015 | Xiang | A24F 40/485 131/328 |
| 2015/0245655 A1* | 9/2015 | Memari | H02J 7/00 206/242 |
| 2015/0313284 A1* | 11/2015 | Liu | A24F 40/50 131/329 |
| 2015/0374040 A1* | 12/2015 | Chen | A24F 40/53 131/328 |
| 2016/0064979 A1* | 3/2016 | Huang | H02J 7/0029 320/114 |
| 2016/0143359 A1 | 5/2016 | Xiang | |
| 2016/0377667 A1 | 12/2016 | Friedrich et al. | |
| 2017/0023648 A1* | 1/2017 | Yamashita | H01M 10/0525 |
| 2017/0027234 A1* | 2/2017 | Farine | A24F 40/53 |
| 2017/0238611 A1* | 8/2017 | Buchberger | A24F 40/485 |
| 2017/0264123 A1* | 9/2017 | Mulawski | H02J 7/00714 |
| 2018/0196107 A1 | 7/2018 | Fleischer et al. | |
| 2019/0245250 A1 | 8/2019 | Sakurai et al. | |
| 2019/0387806 A1 | 12/2019 | Nakano et al. | |

FOREIGN PATENT DOCUMENTS

| | | |
|---|---|---|
| CN | 204070534 U | 1/2015 |
| CN | 104473331 A | 4/2015 |
| CN | 208016909 U | 10/2018 |
| CN | 108780916 A | 11/2018 |
| JP | 07-183050 A | 7/1995 |
| JP | 2016-510970 A | 4/2016 |
| JP | 2017-514463 A | 6/2017 |
| WO | 2016/023711 A1 | 2/2016 |
| WO | 2018/167818 A1 | 9/2018 |

OTHER PUBLICATIONS

Decision to Grant a Patent received for Japanese Patent Application No. 2018-244967, dated Oct. 1, 2019, 5 pages including English Translation.

Eurasian Notification dated Mar. 20, 2020 in Eurasian Application No. 201992848/26.

European Search Report dated May 18, 2020, issued in corresponding European Patent Application No. 19219826.5, 5 pages.

Operating Manual Dicodes: "2395/2395T Bedienungsanleitung", Sep. 21, 2016 (Sep. 21, 2016), pp. 1-14, XP055693155, dicodes website Retrieved from the Internet:URL:https://www.dicodes-mods.de/dicodes-2395.html [retrieved on May 8, 2020] * p. 3-p. 12 *.

Taiwanese Office Action dated Jul. 16, 2020, issued in corresponding Taiwanese Patent Application No. 108147610.

Communication pursuant to Article 94(3) dated Jun. 9, 2020, issued in corresponding European Patent Application 19219826.5.

Office Action dated Feb. 23, 2021, in corresponding Chinese patent Application No. 201911373208.7, 47 pages.

* cited by examiner

POWER SUPPLY UNIT FOR AEROSOL INHALER, AND CONTROL METHOD AND CONTROL PROGRAM OF THE SAME

CROSS-REFERENCE TO RELATED APPLICATIONS

This application is based upon and claims the benefit of priority from prior Japanese patent application No. 2018-244967, filed on Dec. 27, 2018, the entire contents of which are incorporated herein by reference.

TECHNICAL FIELD

The present invention relates to a power supply unit for an aerosol inhaler, and a control method and control program of the power supply unit.

BACKGROUND ART

An aerosol generating device disclosed in Patent Literature 1 measures the voltage between the terminals of an electric energy supply source in the course of use of the aerosol generating device, and monitors whether the corresponding voltage is lower than a threshold for the voltage at an arbitrary time point by comparing it with the threshold. However, by only measuring voltage drop, it is not possible to determine whether it is just required to recharge the battery, or the battery has deteriorated so much that replacement is required. For this reason, the aerosol generating device disclosed in Patent Literature 1 tracks voltage drop from the status of the usage record, and issues a signal when battery replacement is required.

Patent Literature 1 JP-T-2017-514463

The aerosol generating device disclosed in Patent Literature 1 can perform determination on deterioration of the battery, but cannot detect a short circuit of the battery. In order to further improve the safety of the aerosol generating device, in the case where an internal short circuit, which means a short circuit which occurs in the power supply, or an external short circuit, which means a short circuit which occurs outside the power supply, occurs, it is desirable to detect the short circuit.

An object of the present invention is to provide a power supply unit for an aerosol inhaler, and a control method and control program of the power supply unit, capable of detecting a short circuit of a power supply.

SUMMARY OF INVENTION

According to an aspect of the invention, there is provided a power supply unit for an aerosol inhaler, the power supply unit comprising: a power supply able to discharge power to a load for generating an aerosol from an aerosol source; a control unit configured to control the power supply; and a sensor configured to output a value related to a remaining amount of the power supply, wherein the control unit detects a short circuit of the power supply based on an output value of the sensor.

BRIEF DESCRIPTION OF DRAWINGS

FIG. 11 is an equivalent circuit diagram equivalent to the electric circuit of the aerosol inhaler of FIG. 5 when the switch is on.

DESCRIPTION OF EMBODIMENTS

Figure 1:
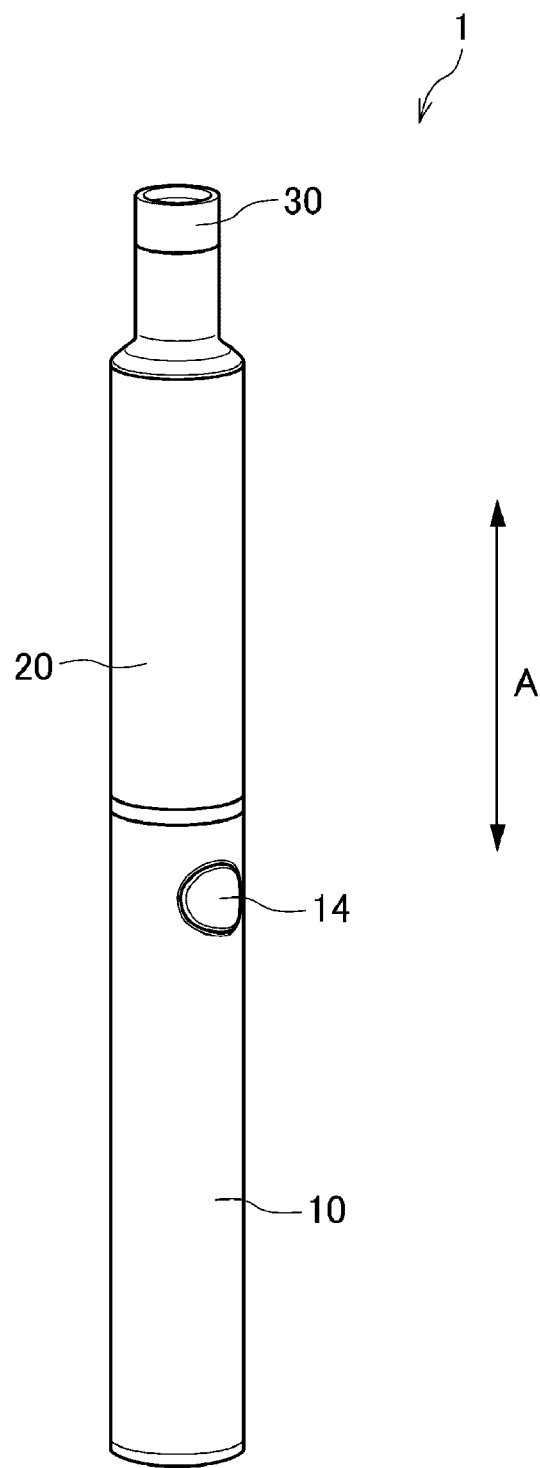
FIG. 1 is a perspective view of an aerosol inhaler equipped with a power supply unit of an embodiment of the present invention.
Figure 2:
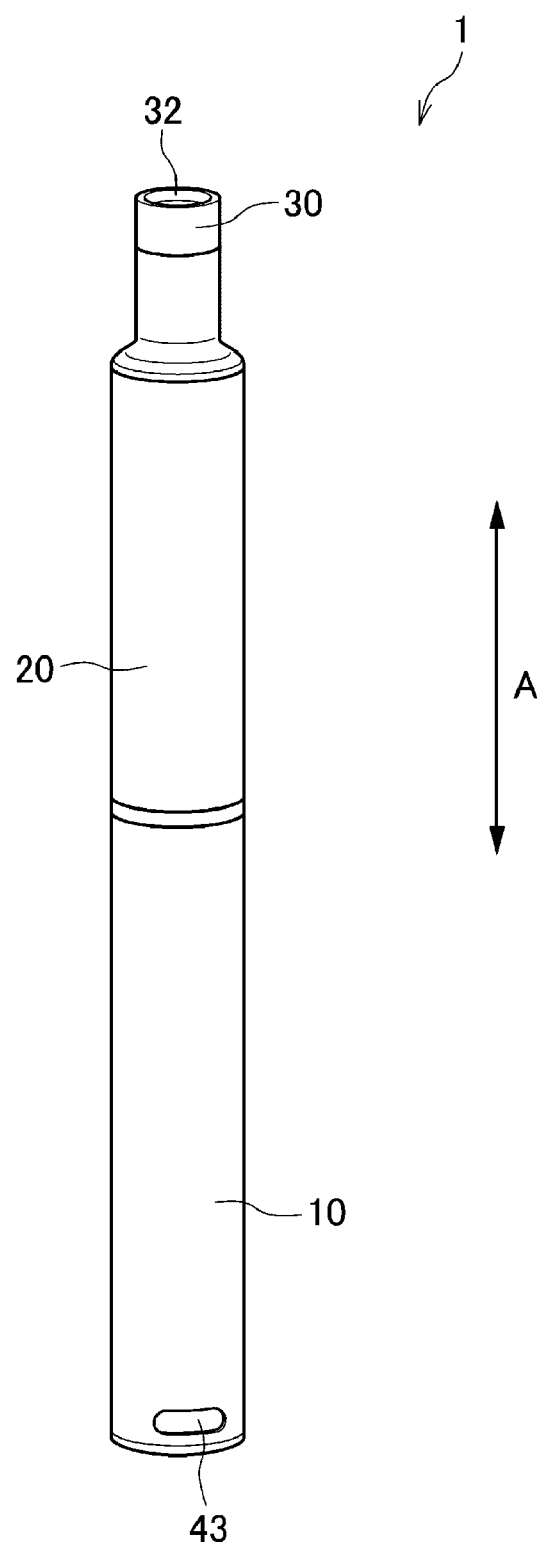
FIG. 2 is another perspective view of the aerosol inhaler of FIG. 1.

Hereinafter, a power supply unit for an aerosol inhaler according to an embodiment of the present invention will be described. First of all, an aerosol inhaler equipped with the power supply unit will be described with reference to FIG. 1 to FIG. 3.

Aerosol Inhaler

An aerosol inhaler 1 is a device for inhaling a flavor without combustion, and has a rod shape extending along a certain direction (hereinafter, referred to as the longitudinal direction A). The aerosol inhaler 1 includes a power supply unit 10, a first cartridge 20, and a second cartridge 30 which are arranged in the order along the longitudinal direction A. The first cartridge 20 can be attached to and detached from the power supply unit 10, and the second cartridge 30 can be attached to and detached from the first cartridge 20. In other words, the first cartridge 20 and the second cartridge 30 can be individually replaced.

Power Supply Unit

Figure 3:
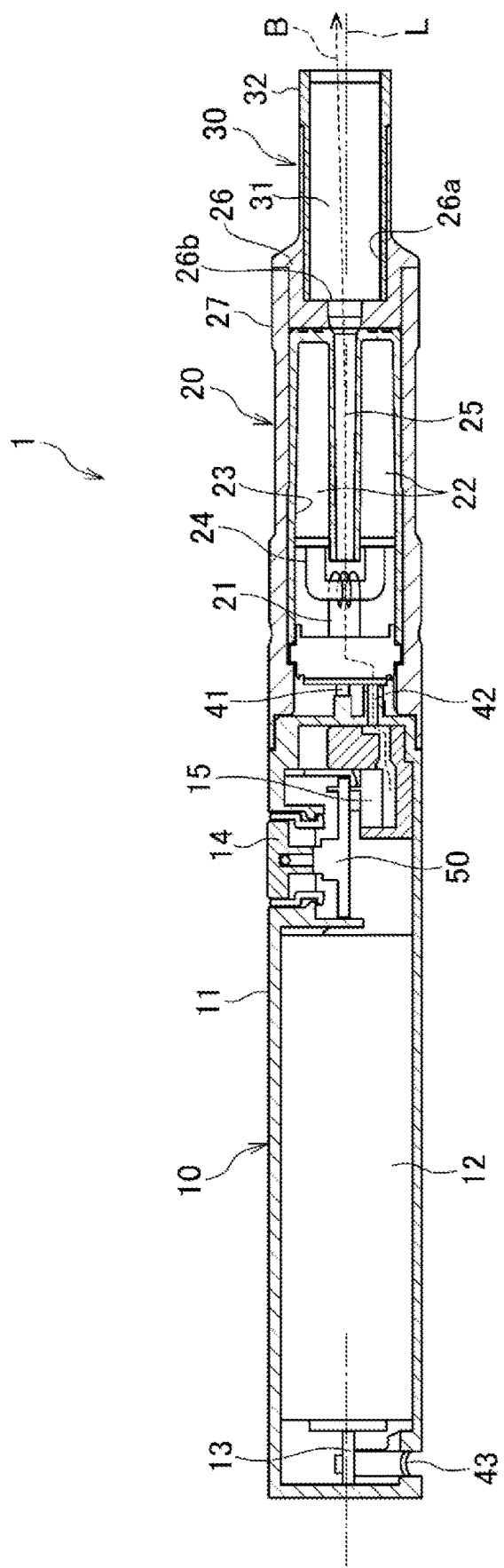
FIG. 3 is a cross-sectional view of the aerosol inhaler of FIG. 1.
Figure 4:
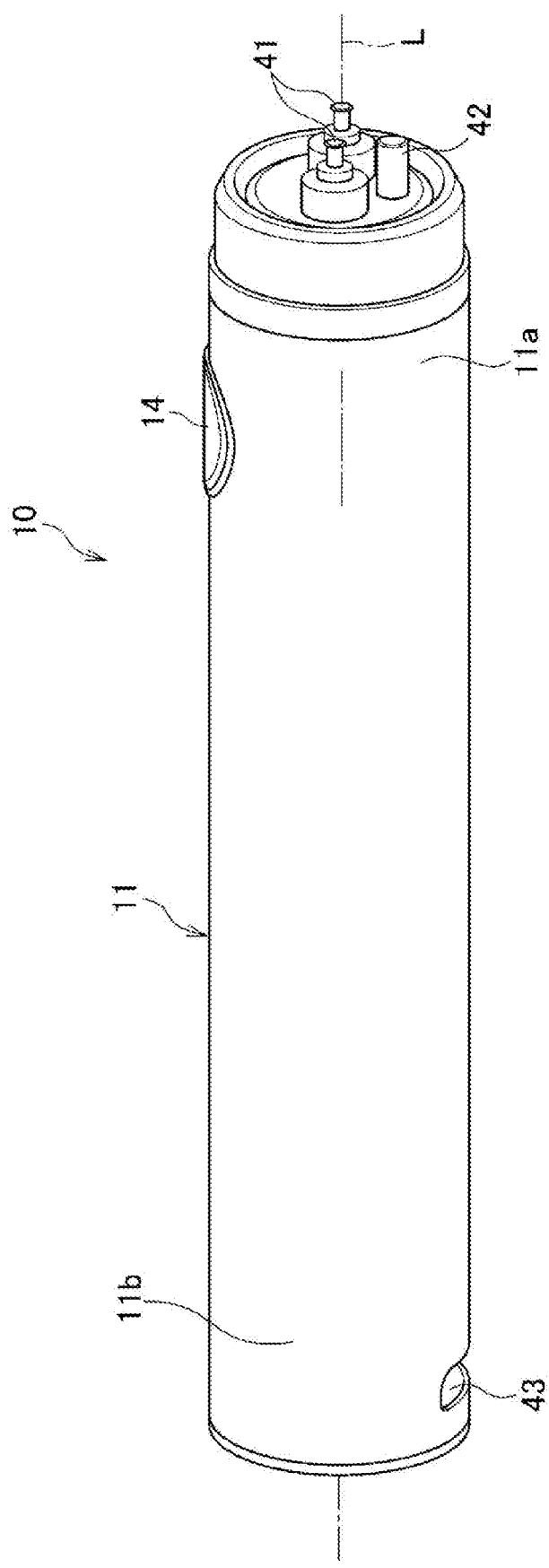
FIG. 4 is a perspective view of the power supply unit.

The power supply unit 10 of the present embodiment includes a power supply 12, a charger 13, a control unit 50, various sensors, and so on in a cylindrical power supply unit case 11, as shown in FIG. 3 and FIG. 4. The power supply 12 is a chargeable secondary battery, an electric double-layer capacitor, or the like, and is preferably a lithium-ion battery.

On a top part 11a of the power supply unit case 11 positioned on one end side in the longitudinal direction A (the first cartridge (20) side), a discharging terminal 41 is provided. The discharging terminal 41 is provided so as to protrude from the top surface of the top part 11a toward the first cartridge 20, and is configured to be able to be electrically connected to a load 21 of the first cartridge 20.

Further, on a part of the top surface of the top part 11a in the vicinity of the discharging terminal 41, an air supply part 42 for supplying air to the load 21 of the first cartridge 20 is provided.

On a bottom part 11b of the power supply unit case 11 positioned on the other end side in the longitudinal direction (the opposite side to the first cartridge 20), a charging terminal 43 able to be electrically connected to an external power supply 60 (see FIG. 5) capable of charging the power supply 12 is provided. The charging terminal 43 is provided on the side surface of the bottom part 11b, such that at least one of USB terminals, micro USB terminals, and lightning terminals can be connected thereto.

However, the charging terminal 43 may be a power receiving part able to receive power from the external power supply 60 in a non-contact manner. In this case, the charging terminal 43 (the power receiving part) may be composed of a power receiving coil. The wireless power transfer system may be an electromagnetic induction type, or may be a magnetic resonance type. Also, the charging terminal 43 may be a power receiving part able to receive power from the external power supply 60 without any contact point. As another example, the charging terminal 43 may be configured such that at least one of USB terminals, micro USB terminals, and lightning terminals can be connected thereto and the above-mentioned power receiving part is included therein.

Also, on the side surface of the top part 11a of the power supply unit case 11, an operation unit 14 which the user can operate is provided so as to face the opposite side to the charging terminal 43. More specifically, the operation unit 14 and the charging terminal 43 are symmetric with respect to the point of intersection of a straight line connecting the operation unit 14 and the charging terminal 43 and the center line L of the power supply unit 10 in the longitudinal direction A. The operation unit 14 is composed of a button type switch, a touch panel, or the like, and is used to perform various processes such as a process of activating and shutting off the control unit 50 and various sensors according to user's intention to use. In the vicinity of the operation unit 14, the control unit 50 and an inhalation sensor 15 for detecting a puff action are provided.

The charger 13 is disposed close to the charging terminal 43, and controls charging power from the charging terminal 43 to be input to the power supply 12. The charger 13 includes a converter for converting direct current, which is applied from an inverter 61 or the like (see FIG. 5) provided for converting alternating current into direct current on a charging cable which is connected to the charging terminal 43, into direct current having a different magnitude, a voltmeter, an ammeter, a processor, and so on.

Figure 6:
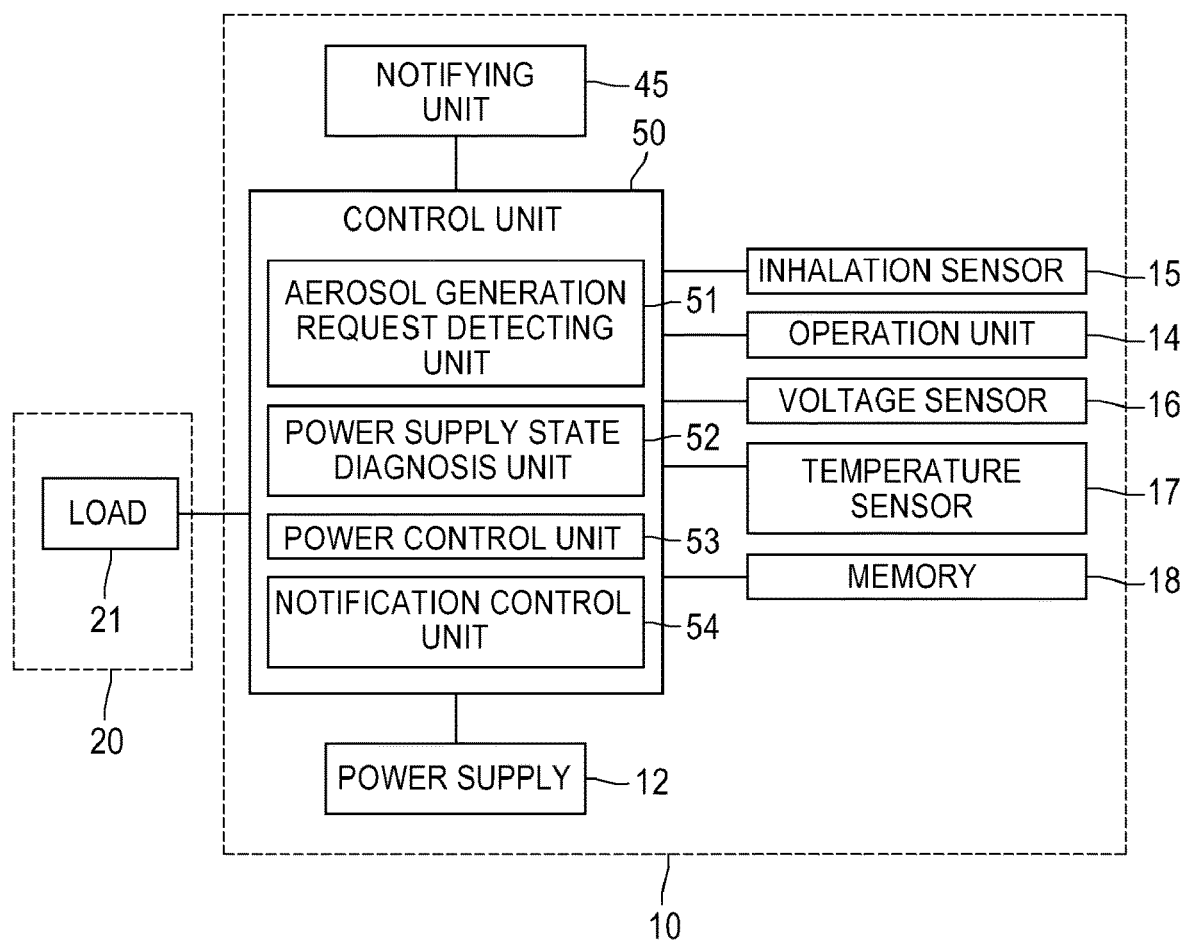
FIG. 6 is a block diagram of the power supply unit.

The control unit 50 is connected to various sensor devices, such as the inhalation sensor 15 for detecting a puff (inhaling) action, a voltage sensor 16 for measuring the voltage of the power supply 12, and a temperature sensor 17, the operation unit 14, and a memory 18 for storing the number of puff actions, the time for which power has been applied to the load 21, and so on, as shown in FIG. 6, and performs a variety of control on the aerosol inhaler 1. The inhalation sensor 15 may be configured with a capacitor microphone, a pressure sensor, or the like. The control unit 50 is specifically a processor (a computer). More specifically, the structure of this processor is an electric circuit configured by combining circuit elements such as semiconductor elements. The details of the control unit 50 will be described below.

Also, in the power supply unit case 11, an air intake (not shown in the drawings) for taking in air is formed. The air intake may be formed around the operation unit 14, or may be formed around the charging terminal 43.

First Cartridge

As shown in FIG. 3, the first cartridge 20 includes a reservoir 23 for storing an aerosol source 22, the electric load 21 for atomizing the aerosol source 22, a wick 24 for drawing the aerosol source from the reservoir 23 toward the load 21, an aerosol channel 25 for an aerosol generated by atomizing the aerosol source 22 to flow toward the second cartridge 30, an end cap 26 for storing a part of the second cartridge 30, inside a cylindrical cartridge case 27.

The reservoir 23 is formed so as to surround the aerosol channel 25, and holds the aerosol source 22. In the reservoir 23, a porous member such as a resin web or cotton may be stored, and the porous member may be impregnated with the aerosol source 22. The aerosol source 22 includes a liquid such as glycerin, propylene glycol, or water.

The wick 24 is a liquid holding member for drawing the aerosol source 22 toward the load 21 using capillarity, and is configured with, for example, glass fiber, a porous ceramic, or the like.

The load 21 atomizes the aerosol source 22 without combustion by power which is supplied from the power supply 12 through the discharging terminal 41. The load 21 is configured with a heating wire wound with a predetermined pitch (a coil). However, the load 21 needs only to be an element capable of atomizing the aerosol source 22, thereby generating an aerosol, and is, for example, a heating element or an ultrasonic wave generator. Examples of the heating element include a heating resistor, a ceramic heater, an induction heating type heater, and so on.

The aerosol channel 25 is provided on the downstream side of the load 21 on the center line L of the power supply unit 10.

The end cap 26 includes a cartridge storage part 26a for storing a part of the second cartridge 30, and a connecting passage 26b for connecting the aerosol channel 25 and the cartridge storage part 26a.

Second Cartridge

The second cartridge 30 holds a flavor source 31. The end part of the second cartridge 30 on the first cartridge (20) side is stored in the cartridge storage part 26a provided in the end cap 26 of the first cartridge 20, so as to be able to be removed. The end part of the second cartridge 30 on the opposite side to the first cartridge (20) side is configured as an inhalation port 32 for the user. However, the inhalation port 32 does not necessarily need to be configured integrally with the second cartridge 30 so as not to be separable from the second cartridge, and may be configured to be able to be attached to and detached from the second cartridge 30. If the inhalation port 32 is configured separately from the power supply unit 10 and the first cartridge 20 as described above, it is possible to keep the inhalation port 32 sanitary.

The second cartridge 30 adds a flavor to the aerosol generated by atomizing the aerosol source 22 by the load 21, by passing the aerosol through the flavor source 31. As a raw material piece which constitutes the flavor source, a compact made by forming shredded tobacco or a tobacco raw material into a grain shape can be used. The flavor source 31 may be configured with a plant (such as mint or a herbal medicine, or a herb) other than tobacco. To the flavor source 31, a flavoring agent such as menthol may be added.

The aerosol inhaler 1 of the present embodiment can generate an aerosol containing the flavor by the aerosol source 22, the flavor source 31, and the load 21. In other words, the aerosol source 22 and the flavor source 31 can be referred to as being an aerosol generation source for generating an aerosol.

The configuration of the aerosol generation source which can be used in the aerosol inhaler 1 is not limited to the configuration in which the aerosol source 22 and the flavor source 31 are configured separately, and may be a configuration in which the aerosol source 22 and the flavor source 31 are formed integrally, a configuration in which the flavor source 31 is omitted and the aerosol source 22 contains a substance which can be contained in the flavor source 31, a configuration in which the aerosol source 22 contains a medical substance or the like instead of the flavor source 31, or the like.

In the aerosol inhaler 1 configured as described above, as shown by an arrow B in FIG. 3, air entering from the intake (not shown in the drawings) formed in the power supply unit case 11 passes through the air supply part 42, and passes near the load 21 of the first cartridge 20. The load 21 atomizes the aerosol source 22 drawn from the reservoir 23 by the wick 24. The aerosol generated by atomizing flows through the aerosol channel 25 together with the air entering from the intake, and is supplied to the second cartridge 30 through the connecting passage 26b. The aerosol supplied to the second cartridge 30 passes through the flavor source 31, whereby the flavor is added, and is supplied to the inhalation port 32.

Also, in the aerosol inhaler 1, a notifying unit 45 for notifying a variety of information is provided (see FIG. 6). The notifying unit 45 may be configured with a light emitting element, or may be configured with a vibrating element, or may be configured with a sound output element. Alternatively, the notifying unit 45 may be a combination of two or more elements of light emitting elements, vibrating elements, and sound output elements. The notifying unit 45 may be provided in any one of the power supply unit 10, the first cartridge 20, and the second cartridge 30; however, it is preferable that the notifying unit be provided in the power supply unit 10. For example, the area around the operation unit 14 is configured to have translucency to permit light which is emitted by a light emitting element such as an LED to pass through.

Electric Circuit

Now, the electric circuit of the power supply unit 10 will be described with reference to FIG. 5

The power supply unit 10 includes the power supply 12, a positive electrode side discharging terminal 41a and a negative electrode side discharging terminal 41b which constitute the discharging terminal 41, a positive electrode side charging terminal 43a and a negative electrode side charging terminal 43b which constitute the charging terminal 43, the control unit 50 which is connected between the positive electrode side of the power supply 12 and the positive electrode side discharging terminal 41a and between the negative electrode side of the power supply 12 and the negative electrode side discharging terminal 41b, the voltage sensor 16 which measures the voltage of the power supply 12, the charger 13 which is disposed on the power transmission path between the charging terminal 43 and the power supply 12, and a switch 19 which is disposed on the power transmission path between the power supply 12 and the discharging terminal 41. The switch 19 is configured with, for example, a MOSFET, and is opened and closed by control of the control unit 50 on the gate voltage. The control unit 50 can determine that the external power supply 60 is connected to the charging terminal 43, for example, based on a variation in small current flowing in the control unit 50.

Figure 5:
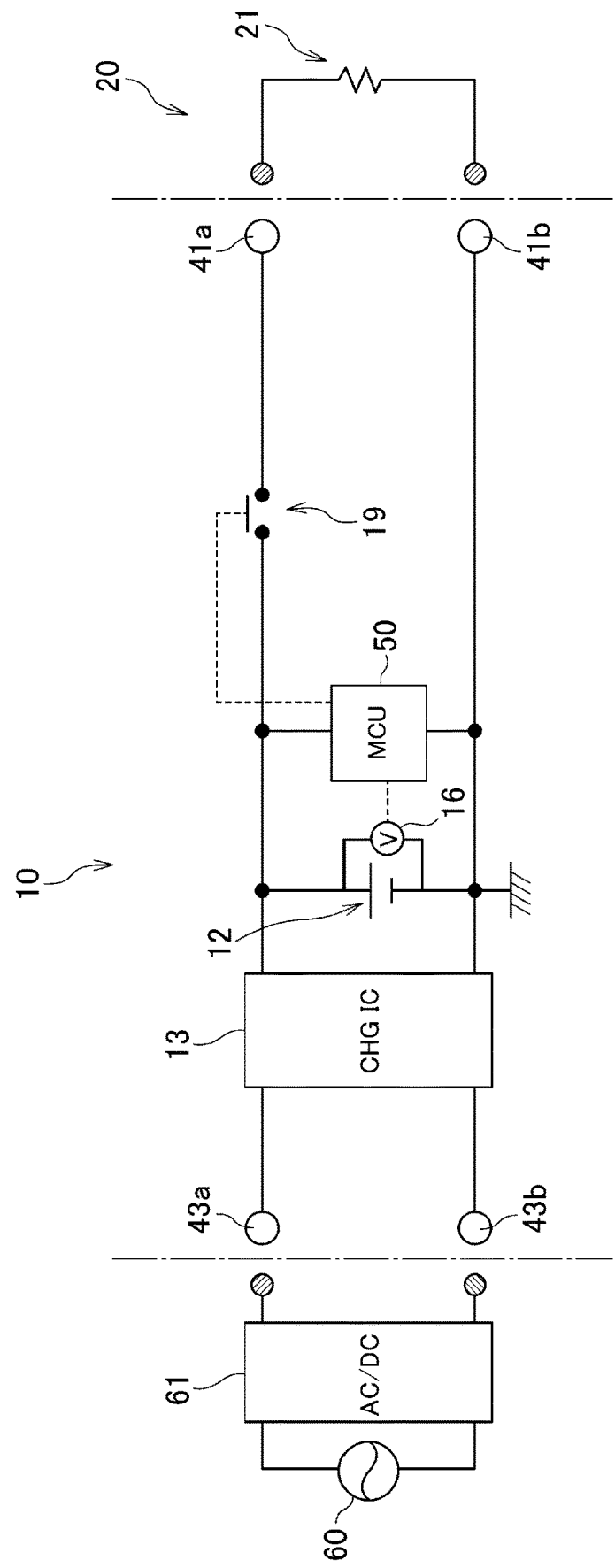
FIG. 5 is an electric circuit diagram of the aerosol inhaler.

In the electric circuit diagram of the power supply unit 10 shown in FIG. 5, the control unit 50 and the voltage sensor 16 are separate parts. Alternatively, the control unit 50 may have the function of measuring the voltage of the power supply 12. Also, in the electric circuit of the power supply unit 10 shown in FIG. 5, the switch 19 is provided between the positive electrode side of the power supply 12 and the positive electrode side discharging terminal 41a. Instead of this so-called plus control type, the switch 19 may be a minus control type which is provided between the negative electrode side discharging terminal 41b and the negative electrode side of the power supply 12.

Control Unit

Now, the configuration of the control unit 50 will be described in more detail.

As shown in FIG. 6, the control unit 50 includes an aerosol generation request detecting unit 51, a power supply state diagnosis unit 52, a power control unit 53, and a notification control unit 54.

The aerosol generation request detecting unit 51 detects a request for aerosol generation based on the output result of the inhalation sensor 15. The inhalation sensor 15 is configured to output the value of a variation in the pressure in the power supply unit 10 caused by inhalation of the user through the inhalation port 32. The inhalation sensor 15 is, for example, a pressure sensor for outputting an output value (for example, a voltage value or a current value) according to atmospheric pressure which varies according to the flow of air which is sucked from the intake (not shown in the drawings) toward the inhalation port 32 (i.e. a puff action of the user).

Figure 7:
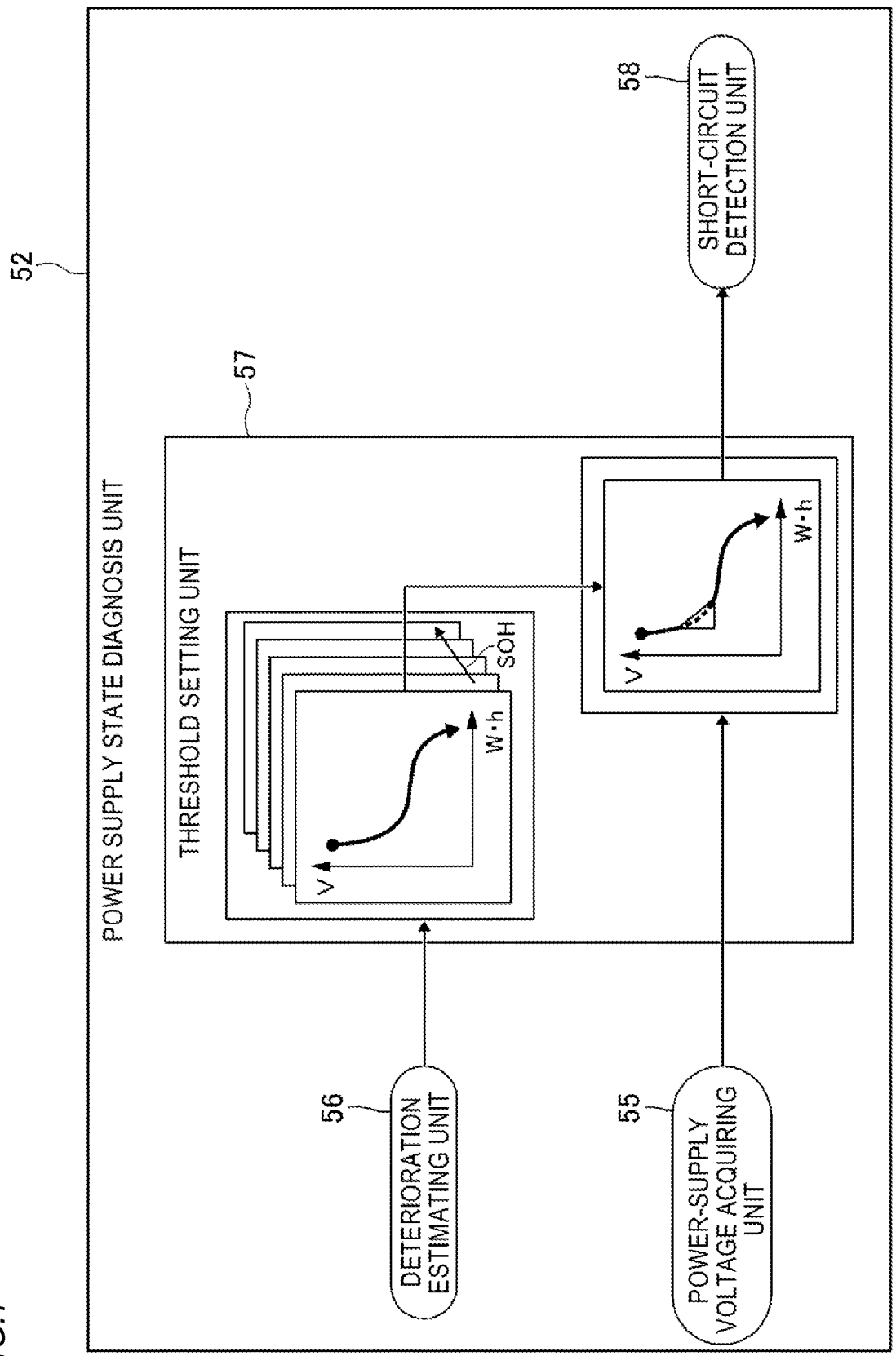
FIG. 7 is a block diagram of a power supply state diagnosis unit.

As shown in FIG. 7, the power supply state diagnosis unit 52 includes a power-supply voltage acquiring unit 55 for acquiring the voltage of the power supply 12 from the voltage sensor 16, a deterioration estimating unit 56 for estimating the state of health of the power supply 12, a threshold setting unit 57 for setting a threshold TH for determining a short circuit of the power supply 12, and a short-circuit detection unit 58 for detecting a short circuit of the power supply 12. The deterioration estimating unit 56 estimates the state of health of the power supply 12 based on the cumulative discharge amount of the power supply 12, the cumulative charging amount of the power supply 12, at least one of the replacement frequencies of the first cartridge 20 and the second cartridge 30, the internal resistance of the power supply 12, or the like. A threshold setting method of the threshold setting unit 57 and short circuit diagnosis control of the short-circuit detection unit 58 will be described below.

Also, the power supply state diagnosis unit 52 can acquire the amount of power stored in the power supply 12, from the voltage of the power supply 12.

The notification control unit 54 controls the notifying unit 45 such that the notifying unit notifies a variety of information. For example, the notification control unit 54 may control the notifying unit 45 such that the notifying unit notifies a short-circuited state, based on diagnosis of the power supply state diagnosis unit 52 on a short circuit of the power supply 12, or may control the notifying unit 45 such that the notifying unit notifies the timing to charge the power supply 12, based on diagnosis of the power supply state diagnosis unit 52 on the amount of charge stored in the power supply 12. Alternatively, the notification control unit 54 may control the notifying unit 45 in response to detection of a timing to replace the second cartridge 30, such that the notifying unit notifies the timing to replace the second cartridge 30. The notification control unit 54 can notify the timing to replace the second cartridge 30, based on the number of puff actions and the cumulative time for which power has been supplied to the load 21, stored in the memory 18.

The power control unit 53 controls discharging of the power supply 12 through the discharging terminal 41 by switching on and off the switch 19 if the aerosol generation request detecting unit 51 detects the request for aerosol generation.

The power control unit 53 performs control such that the amount of aerosol which is generated by atomizing the aerosol source by the load 21 falls in a desired range, i.e. such that the amount of power or the power which is supplied from the power supply 12 to the load 21 falls in a predetermined range. Specifically, the power control unit 53 controls switching on and off of the switch 19 by, for example, PWM (Pulse Width Modulation) control. Alternatively, the power control unit 53 may control switching on and off of the switch 19 by PFM (Pulse Frequency Modulation) control.

The power control unit 53 may stop supply of power from the power supply 12 to the load 21, such that supply of power to the load 21 does not exceed a predetermined period during one puff action. In other words, even while the user is actually performing a puff action, if the puff period exceeds a certain period (hereinafter, referred to as the maximum power supply time), the power control unit 53 stops supply of power from the power supply 12 to the load 21. The maximum power supply time is determined to suppress variation in user's puff period. The maximum power supply time is determined such that the amount of aerosol which is generated during one puff action falls in a desired range. The power control unit 53 controls the on/off duty ratio of the switch 19 for one puff action, according to the amount of power stored in the power supply 12. For example, the power control unit 53 controls the interval between ON periods in which power is supplied from the power supply 12 to the load 21 (see the pulse interval T1 in FIG. 15 and FIG. 17) and controls the length of each ON period in which power is supplied from the power supply 12 to the load 21 (see the pulse width T2 in FIG. 15 and FIG. 17). Also, the interval between ON periods corresponds to the length of an OFF period.

Also, the power control unit 53 detects an electric connection between the charging terminal 43 and the external power supply 60, and controls charging of the power supply 12 through the charging terminal 43.

Here, in the power supply 12 which is used in the aerosol inhaler 1, an internal short circuit meaning a short circuit which occurs in the power supply 12 or an external short circuit meaning a short circuit which occurs outside the power supply 12 may occur. If a short circuit occurs, even in a period in which the power supply should be usable, the amount of charge stored in the power supply 12 may become insufficient, or in some cases, the power supply may become unusable. For this reason, it is required to appropriately grasp a short-circuited state of the power supply 12.

Short Circuit Diagnosis Control

Therefore, the power supply state diagnosis unit 52 detects a short circuit of the power supply 12 by short circuit diagnosis control to be described below. Some types of short circuit diagnosis control to be described below may be configured as programs which can execute them, and be read into the power supply unit 10, and be executed by the power supply unit 10.

The short-circuit detection unit 58 of the power supply state diagnosis unit 52 detects a short circuit of the power supply 12 based on the voltage of the power supply 12 which is the output value of the voltage sensor 16. Specifically, the short-circuit detection unit 58 of the power supply state diagnosis unit 52 detects a short circuit of the power supply 12 from a voltage drop of the power supply 12 which occurs during discharging, based on the voltage of the power supply 12 before discharging (hereinafter, referred to as the pre-discharging voltage) and the voltage of the power supply 12 after discharging (hereinafter, referred to as the post-discharging voltage). Discharging for short circuit detection may be discharging from the power supply 12 to the load 21 for atomizing the aerosol source 22, or may be discharging to an element different from the load 21, for example, a light emitting element, a sound output element, a vibrating element, or the like constituting the notifying unit 45. In the following description, discharging from the power supply 12 to the load 21 will be described as an example.

The short-circuit detection unit 58 of the power supply state diagnosis unit 52 compares the difference between the pre-discharging voltage and the post-discharging voltage with the threshold TH set by the threshold setting unit 57, and detects a short circuit of the power supply 12 in the case where the difference between the pre-discharging voltage and the post-discharging voltage is larger than the threshold TH. Here, the threshold TH is set based on the amount of change in the voltage of the power supply 12 which is caused by discharging. When a short circuit has not occurred in the power supply 12, the difference between the pre-discharging voltage and the post-discharging voltage becomes equal to or smaller than the threshold TH which is set based on the voltage of the power supply 12 according to discharging. However, in the case where a short circuit occurs in the power supply 12, the difference between the pre-discharging voltage and the post-discharging voltage becomes larger, so the difference between the pre-discharging voltage and the post-discharging voltage becomes larger than the threshold TH. Therefore, the short-circuit detection unit 58 can detect a short circuit of the power supply 12 when the difference between the pre-discharging voltage and the post-discharging voltage is larger than the threshold TH.

Now, the method of setting the threshold TH which is performed by the threshold setting unit 57 will be described.

In order to set the threshold TH which is the amount of change in the voltage of the power supply 12 attributable to discharging, the amount of power during discharging may be estimated, and the voltage drop may be acquired from the amount of power estimated.

For example, the actual value of the amount of power which is supplied during one puff action in the case where the power control unit 53 provides power in response to the aerosol generation request may be used as the amount of power, and from this amount of power, the voltage drop may be acquired.

The case shown in FIG. 8A where the power control unit 53 supplies power in response to the aerosol generation request will be described. In the case of performing constant power control for controlling the electric circuit such that power per unit time which is supplied to the load 21 becomes constant, or such that variation in power per unit time which is supplied to the load 21 is suppressed, the amount of power discharged is calculated based on the time for which discharging has been performed, by multiplying a power value during the constant power control by the time for which discharging has been performed. Then, from the amount of power calculated, the voltage drop may be acquired. The amount of discharged power may be obtained by multiplying the sum of times when the switch 19 has been on by the controlled power value. Alternatively, the amount of discharged power may be obtained by multiplying the time from when the switch 19 was turned on for the first time in response to the aerosol generation request to when the switch 19 is turned off lastly by the average value or effective value of power supplied for that time.

Now, the case shown in FIG. 8B where the power control unit 53 supplies power in response to the aerosol generation request will be described. In the case of performing the above-described constant power control, in order to control the electric circuit such that the time when discharging is performed does not exceed the maximum power supply time, on the assumption that constant power has been discharged only for the maximum power supply time, the amount of discharged power is calculated by multiplying the value of power supplied during constant power control by the maximum power supply time. Then, from the amount of power calculated, the voltage drop may be acquired. As the value of power which is supplied during the maximum power supply time, the average value or effective value of power which is supplied after the switch 19 is turned on for the first time until the switch 19 is turned off lastly may be used.

Now, the case shown in FIG. 8C where the power control unit 53 supplies power in response to the aerosol generation request will be described. In the case of controlling the electric circuit such that the time when discharging is performed does not exceed the maximum power supply time, without performing the above-described constant power control, on the assumption that the maximum power which can be supplied to the load 21 has been discharged to the load 21 only for the maximum power supply time, the amount of discharged power is calculated by multiplying the maximum power by the maximum power supply time. Then, from the amount of power calculated, the voltage drop may be acquired. The maximum power may be power in the case where the maximum power (for example, the full charging voltage) which the power supply 12 can apply to the load 21 has been applied.

The threshold setting unit 57 sets a threshold TH based on the voltage drop obtained in the above-described way. The threshold setting unit 57 may correct a predetermined threshold TH based on the voltage drop obtained in the above-described way, instead of setting a threshold TH based on the voltage drop.

Figure 8A:
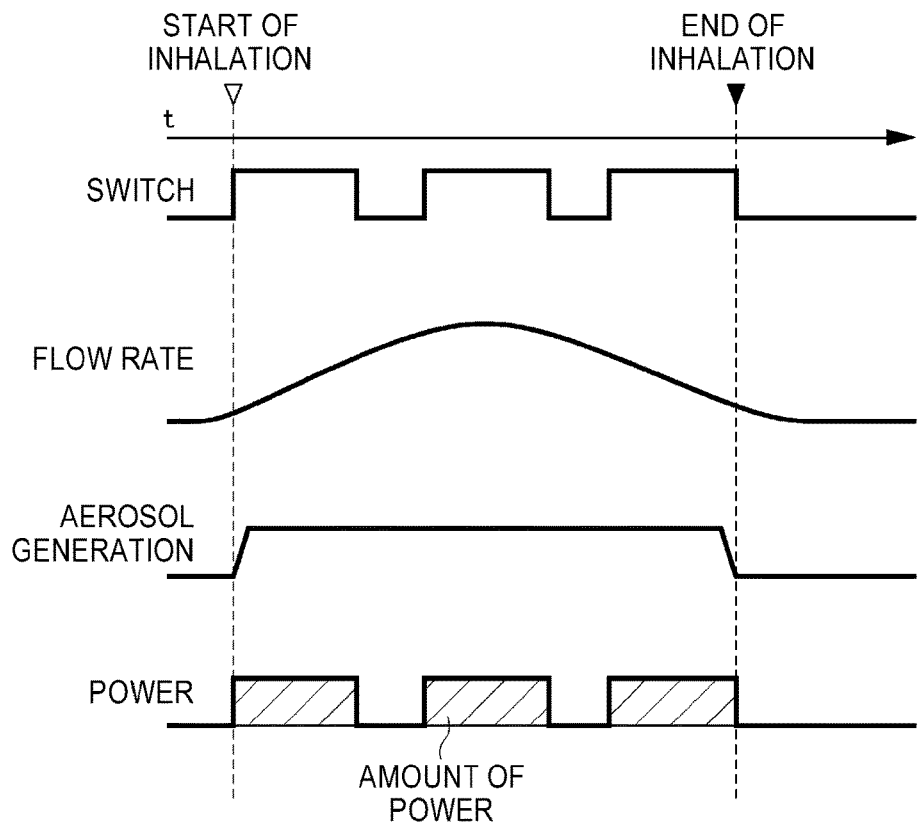
FIG. 8A is a timing chart of an aerosol generation pattern of a first example.
Figure 8B:
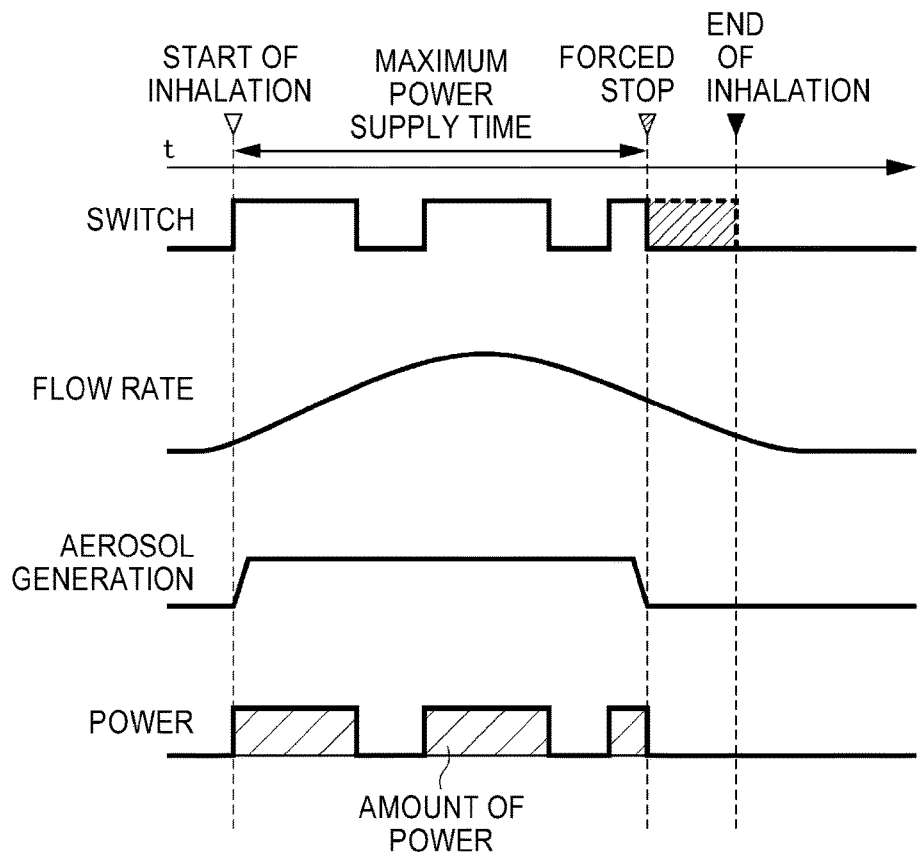
FIG. 8B is a timing chart of an aerosol generation pattern of a second example.
Figure 8C:
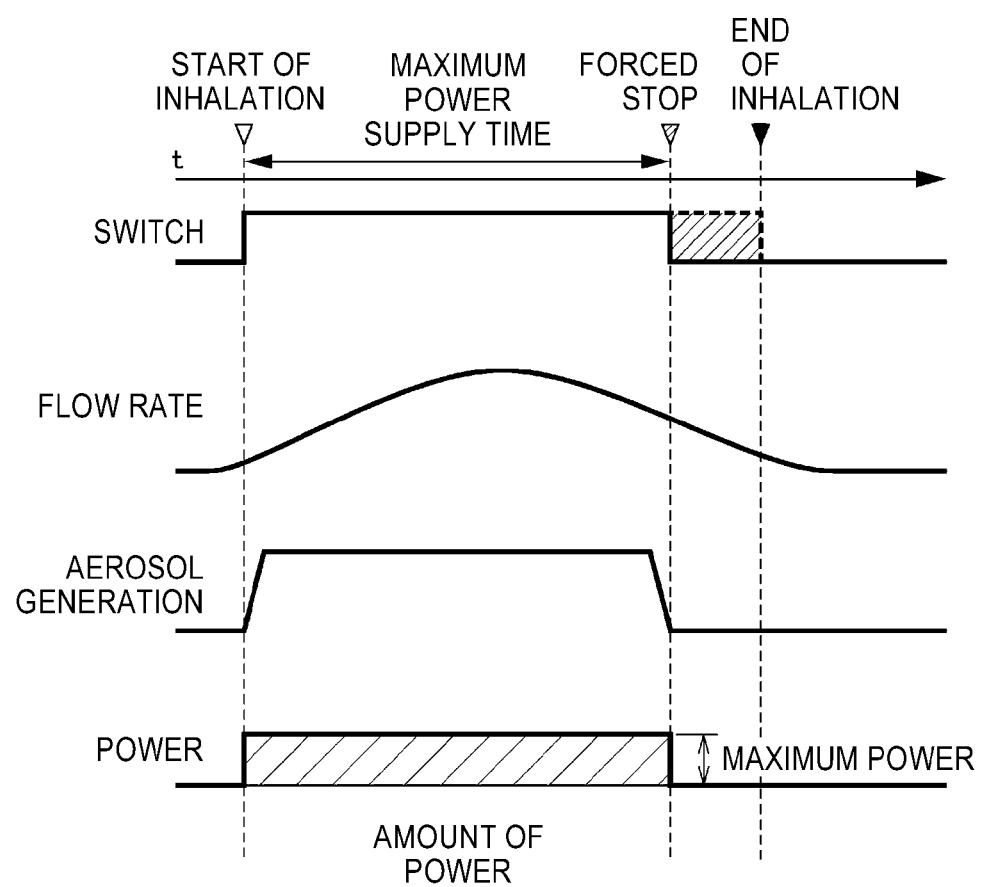
FIG. 8C is a timing chart of an aerosol generation pattern of a third example.

The embodiments shown in FIG. 8A, FIG. 8B, and FIG. 8C are different in the method of setting or correcting the threshold TH as compared. In the embodiment shown in FIG. 8A, in order to set or correct the threshold TH, it is required to acquire the time for which discharging has been performed, and perform the constant power control. In the embodiment shown in FIG. 8B, in order to set or correct the threshold TH, it is required to perform the constant power control. In the embodiment shown in FIG. 8C, not only acquisition of the time for which discharging has been performed but also the constant power control is required. As described above, in the embodiment shown in FIG. 8A, based on the accurate actual value of the amount of power which is supplied during one puff action, the threshold TH is set or corrected. Therefore, the accuracy of short circuit diagnosis improves. Meanwhile, in the embodiment shown in FIG. 8C, any special processing is not required for setting or correcting the threshold TH. Therefore, it is possible to easily perform short circuit diagnosis.

In the embodiments shown in FIG. 8A and FIG. 8B, the voltage is applied to the load 21 only when the switch 19 is on. Here, it should be noted that in the electric circuit shown in FIG. 5, if a smoothing capacitor having a sufficient size is connected in parallel with the power supply 12 between the switch 19 and the positive electrode side discharging terminal 41a, even when the switch 19 is off, the voltage is applied to the load 21. It will be understood that, in this case, in calculating the amount of discharged power, it is especially effective to use the time from when the switch 19 is turned on for the first time in response to the aerosol generation request to when the switch 19 is turned off lastly, and the average value or effective value of power which is supplied for that time.

Now, discharge performance of the power supply 12 will be described.

Figure 9:
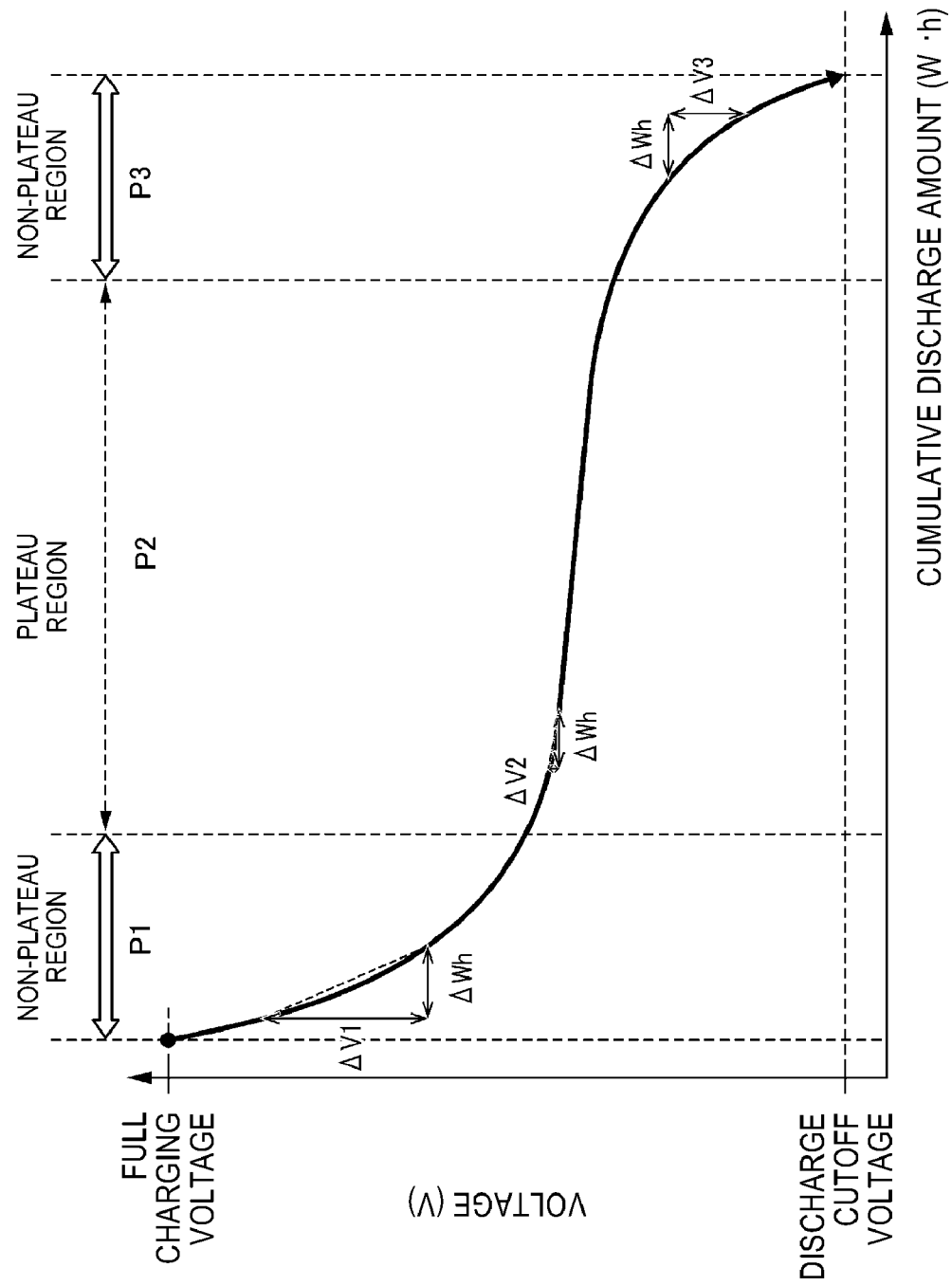
FIG. 9 is a view illustrating a general battery discharge curve.

FIG. 9 is a general battery discharge curve obtained by taking voltage (V) on the vertical axis and the cumulative discharge amount (W·H) on the horizontal axis. As shown in FIG. 9, of a region in which the voltage of the power supply 12 is divided by the full charging voltage and the discharge cutoff voltage, in a region P1 in which the cumulative discharge amount is small and a region P3 in which the cumulative discharge amount is large (hereinafter, this regions P1 and P3 will be referred to as the non-plateau regions P1 and P3), the amount of change of the voltage of the power supply 12 per unit discharge amount (the degree of change) becomes large. Meanwhile, in a region P2 between the region P1 in which the cumulative discharge amount is small and the region P3 in which the cumulative discharge amount is large (hereinafter, this region P2 will be referred to as the plateau region), the amount of change of the voltage of the power supply 12 per unit discharge amount (the degree of change) becomes small.

Therefore, in setting the threshold TH based on the voltage drop, it is required to consider the discharge characteristic of the power supply 12. In other words, in the non-plateau regions P1 and P3, the voltage drops relative to an amount of power $\Delta Wh$ are $\Delta V1$ and $\Delta V3$, respectively; whereas in the plateau region P2, the voltage drop relative to the amount of power $\Delta Wh$ is 66 V2 significantly smaller than $\Delta 1$ and $\Delta 3$.

Therefore, if the threshold TH is always set based on the voltage drop $\Delta 2$ relative to the amount of power $\Delta Wh$ which is caused by discharging, even though the voltage of the power supply 12 changes, a short circuit of the power supply 12 may be erroneously detected even though a short circuit of the power supply 12 has not occurred. Therefore, it is desirable for the threshold setting unit 57 to set the threshold TH based on the degree of change of the voltage of the power supply 12 which is obtained in the case where the voltage of the power supply 12 belongs to the non-plateau regions P1 and P3 of the region which is defined by the full charging voltage and the discharge cutoff voltage, and it is more desirable to set the threshold based on the degree of change of the voltage of the power supply 12 which is obtained in the case where the voltage of the power supply 12 belongs to the region in which the amount of change of the voltage of the power supply 12 per unit discharge amount is largest (for example, the non-plateau region P1), of the region which is divided by the full charging voltage and the discharge cutoff voltage. In the case of setting the threshold TH in the above-described way, it is unnecessary to change the threshold TH according to the voltage of the power supply 12, and it is possible to prevent erroneous detection.

Also, the threshold setting unit 57 may set or correct the threshold TH according to the voltage of the power supply 12. In this case, although calculation of the threshold TH becomes complicated, it becomes possible to set a more appropriate threshold TH. Further, since the voltage drop relative to the amount of power ΔWh changes according to the state of health of the power supply 12, the threshold setting unit 57 may set or correct the threshold TH according to the state of health of the power supply 12. In this case, it is possible to set an optimal threshold TH according to the state of the power supply 12, and the accuracy of short circuit detection improves.

With reference to FIG. 7 and FIG. 9, setting of an optimal threshold TH will be described in detail. The discharge curve shown in FIG. 9 and described above changes according to the state of health of the power supply 12. Therefore, discharge curves according to the states of health are stored in the threshold setting unit 57 in advance. The threshold setting unit 57 selects an optimal discharge curve based on the state of health which is inputted from the deterioration estimating unit 56. Also, the threshold setting unit 57 needs only to set the actual value of the amount of power which is supplied during one puff action, a voltage drop, and a threshold TH, based on the power-supply voltage and the optimal discharge curve which are inputted from the power-supply voltage acquiring unit 55.

As described above, the short-circuit detection unit 58 of the power supply state diagnosis unit 52 detects a short circuit of the power supply 12 based on the voltage of the power supply 12 which is the output value of the voltage sensor 16, and the voltage of the power supply 12 may be open circuit voltage OCV, or may be closed circuit voltage CCV. Here, the open circuit voltage OCV and closed circuit voltage CCV of the power supply 12 will be described taking as an example the case where the power supply 12 is a lithium-ion battery.

Figure 10:
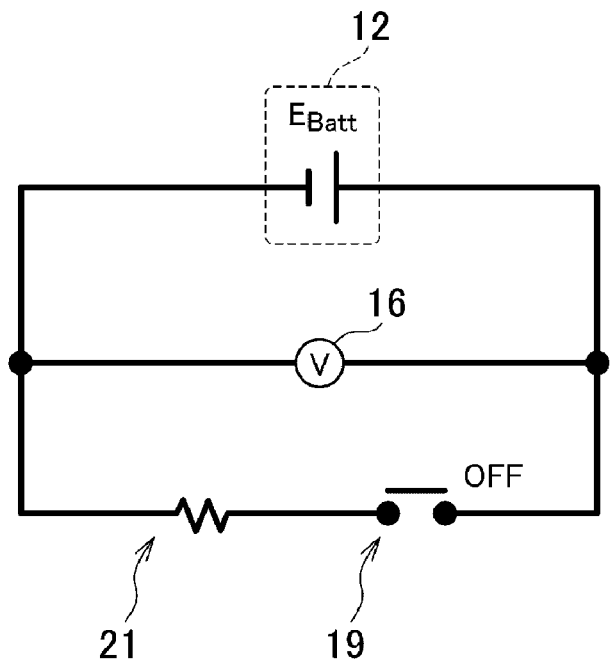
FIG. 10 is an electric circuit diagram simply illustrating the electric circuit diagram of the aerosol inhaler of FIG. 5 when a switch is off.

FIG. 10 is a view simply illustrating the electric circuit diagram of the aerosol inhaler 1 of FIG. 5 when the switch 19 is off. The measurement value of the voltage sensor 16 when the switch 19 is off, i.e. the open circuit voltage OCV is equal to the electromotive force $E_{Batt}$ of the power supply 12.

Figure 11:
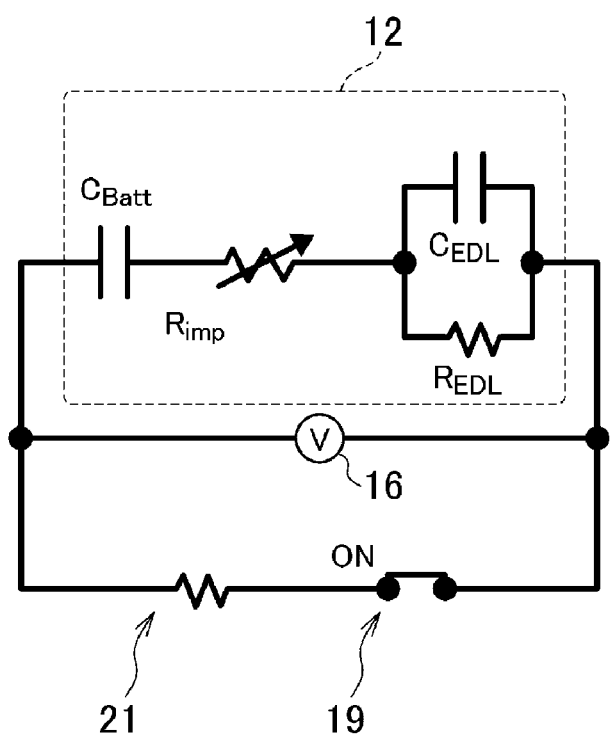

FIG. 11 is a view illustrating a circuit equivalent to the electrical circuit of the aerosol inhaler 1 of FIG. 5 when the switch 19 is on (when the electric circuit constitutes a closed circuit). A reference symbol "$C_{Batt}$" represents a capacitor having the same electromotive force as that of the power supply 12, and a reference symbol "$R_{imp}$" represents the inter-electrode internal resistance between the electrodes which is applied to lithium ions when the lithium ions move between the electrodes, and a reference symbol "$C_{EDL}$" represents a capacitor showing electric double-layer capacitance at the electrode interfaces, and a reference symbol "$R_{EDL}$" represents reaction resistance when lithium ions move in the interfaces between the electrodes and the electrolytic solution. The reaction resistance $R_{EDL}$ and the electric double-layer capacitor $C_{EDL}$ are provided in parallel on the downstream side of the capacitor $C_{Batt}$ and the inter-electrode internal resistance $R_{imp}$, whereby the inter-electrode internal resistance $R_{imp}$ constitutes a direct current (DC) component, and the reaction resistance $R_{EDL}$ constitutes a primary delay (AC) component.

The measurement value of the voltage sensor 16 when the switch 19 is on, i.e. the closed circuit voltage CCV is the value obtained by subtracting a loss caused by the inter-electrode internal resistance $R_{imp}$ and a loss caused by the reaction resistance $R_{EDL}$ from the electromotive force of the power supply 12.

Figure 12:
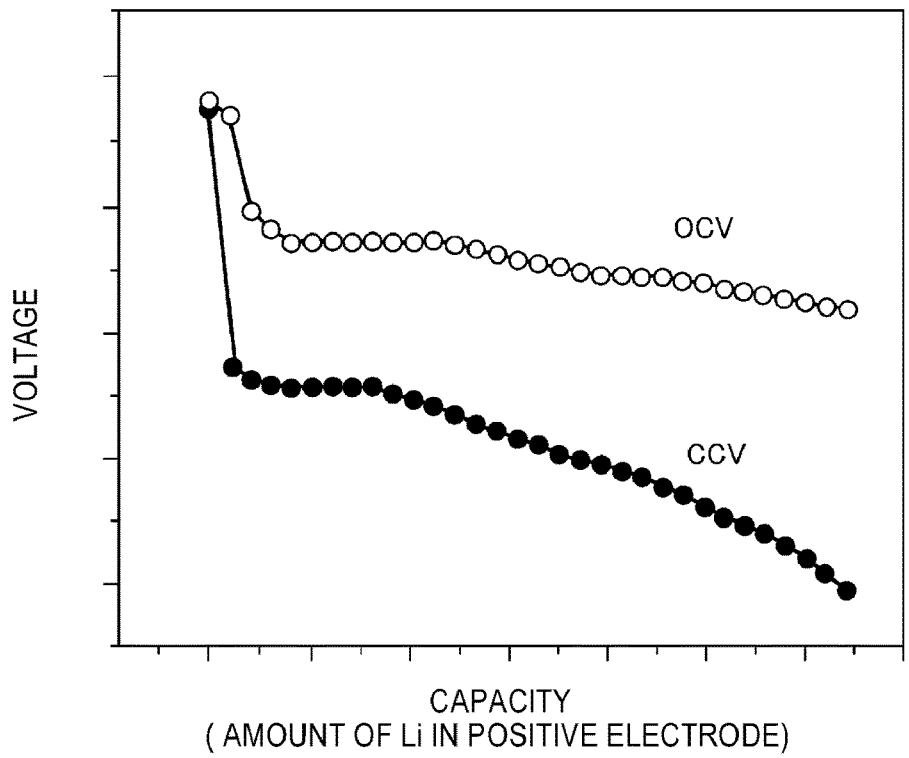
FIG. 12 is a graph illustrating the relation of open circuit voltage, closed circuit voltage, and the remaining amount of a power supply.
Figure 13:
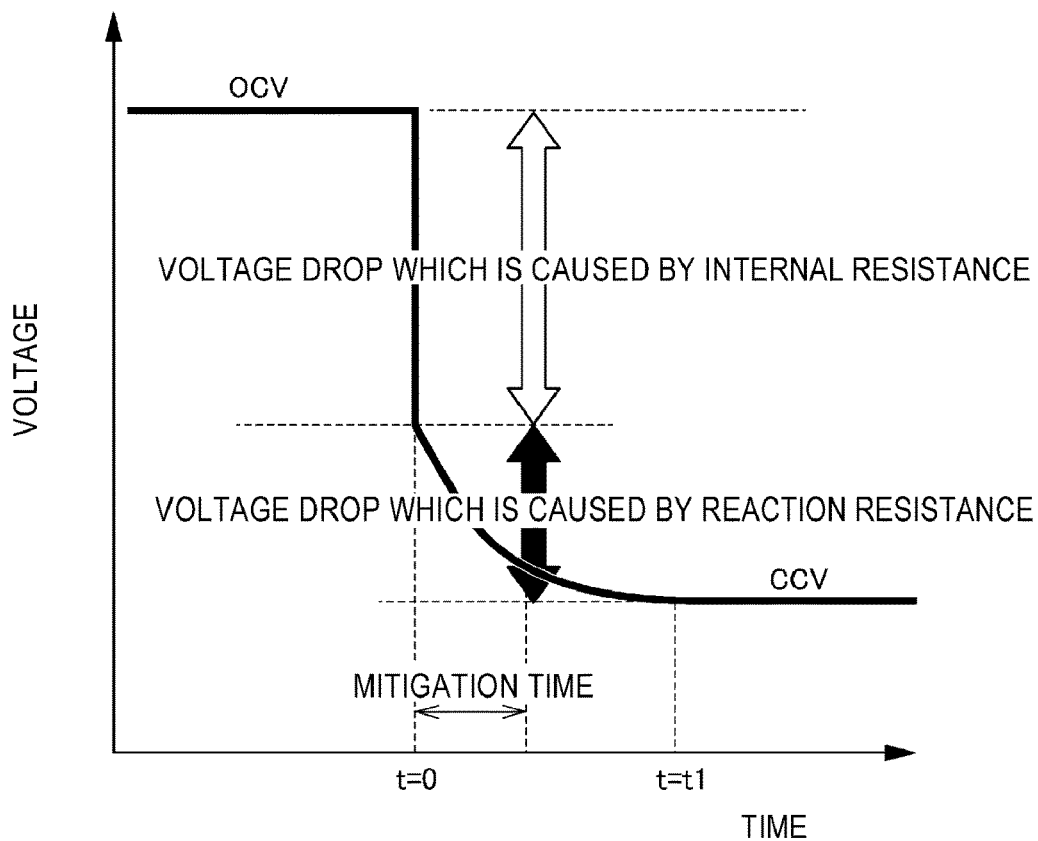
FIG. 13 is an explanatory view for explaining the relation between the difference between the open circuit voltage and the closed circuit voltage and internal resistance.

Therefore, as shown in FIG. 12, with respect to the same remaining amount of the power supply 12, the relation in which the open circuit voltage OCV is larger than the closed circuit voltage CCV is established. FIG. 12 shows the relation between the open circuit voltage OCV and the closed circuit voltage CCV according to discharging of a lithium-ion secondary battery using spinel-type $Li_{1+x}Co_2O_4$ as its positive-electrode active material, disclosed in LITHIUM COBALT SPINEL OXIDE: A STRUCTURAL AND ELECTROCHEMICAL STUDY (ERIKA MEZA et al, J. Chil. Chem. Soc, 53, No 2 (2008), pages: 1494-1497). The vertical axis represents the voltage values of the open circuit voltage OCV and the closed circuit voltage CCV, and as it goes upward, the voltage values increase. The horizontal axis represents the amount of lithium in the positive-electrode active material, and as it goes more to the right, the amount increases. In other words, as it goes more to the right, the remaining power storage capacity decreases, and the integrated value of discharged power increases.

The temporal change of the closed circuit voltage CCV in the equivalent circuit shown in FIG. 11 can be expressed as the following Expression (1) and Expression (2).

$$CCV(t) = E_{Batt} - I(t) \cdot R_{imp.} - I(t) \cdot R_{EDL} \cdot \left\{1 - \exp\left(-\frac{t}{R_{EDL} \cdot C_{EDL}}\right)\right\} \quad (1)$$

$$I(t) = \frac{E_{Batt}}{R_{imp.} + R_{EDL} \cdot \left\{1 - \exp\left(-\frac{t}{R_{EDL} \cdot C_{EDL}}\right)\right\} + R_{load}} \quad (2)$$

In Expression (2), $R_{load}$ represents the electric resistance value of the load 21.

Immediately after the switch 19 is turned on, the reaction resistance $R_{EDL}$ which is the primary delay component is negligible. In other words, immediately after the switch 19 is turned on, i.e. when t is 0, the difference between the open circuit voltage OCV and the closed circuit voltage CCV depends on the voltage drop which is caused by the inter-electrode internal resistance $R_{imp}$.

This can be expressed as Expression (3) from Expression (1) and Expression (2).

$$\frac{OCV - CCV(0)}{I(0)} = R_{imp.} \quad (3)$$

Meanwhile, in the case where t is sufficiently larger than the product of primary delay component mitigation times (time constants) $R_{EDL}$ and $C_{EDL}$ shown in Expression (1) and Expression (2), the difference between the open circuit voltage OCV and the closed circuit voltage CCV is attributable to the sum of the voltage drop caused by the inter-electrode internal resistance $R_{imp}$ and the voltage drop caused by the reaction resistance $R_{EDL}$.

This can be expressed as Expression (4) from Expression (1) and Expression (2).

$$\frac{OCV - CCV(t)}{I(t)} = R_{imp.} + R_{EDL} \quad (4)$$

By the way, in general, $R_{EDL}$ and $C_{EDL}$ are sufficiently small values. Therefore, it should be noted that the relation of Expression (4) is (approximately) established at a relatively early timing after the switch 19 is closed.

In the case of using closed circuit voltage CCV, the closed circuit voltage may be an output value which is obtained when a sufficient time passes (t=t1) after the circuit is closed, or may be an output value which is obtained before the sufficient time passes (t<t1) after the circuit is closed. The time t1 is set based on the time constant (the product of $R_{EDL}$ and $C_{EDL}$) in the case where change of the closed circuit voltage CCV is considered in a primary delay system. By the way, as described above, the closed circuit voltage CCV changes according to the elapsed time after the circuit is closed due to the reaction resistance $R_{EDL}$ which is a primary delay (AC) component. Therefore, as for the pre-discharging voltage and the post-discharging voltage, it is required to match the timings to acquire them after a predetermined period including 0 passes from when a closing instruction is sent to the switch 19.

If the timings are not matched, the reaction resistances of the pre-discharging voltage and the post-discharging voltage are different. Therefore, this reaction resistance difference is mixed as noise in the difference between the pre-discharging voltage and the post-discharging voltage, so the accuracy of short circuit diagnosis decreases. By using the output value which is obtained before the sufficient time passes after the circuit is closed, as the closed circuit voltage CCV, it is possible to acquire the closed circuit voltage CCV earlier. Meanwhile, by using the output value which is obtained when the sufficient time passes after the circuit is closed, as the closed circuit voltage CCV, it is possible to more accurately acquire the closed circuit voltage CCV.

Also, when acquiring the closed circuit voltage CCV, the power supply state diagnosis unit 52 may acquire the closed circuit voltage CCV using current smaller than the current when power is discharged to the load 21 in order to generate an aerosol. By acquiring the closed circuit voltage CCV using small current, it is possible to restrain an aerosol from being generated during acquisition of the closed circuit voltage CCV.

Now, the control flow of the short circuit diagnosis control which is performed by the short-circuit detection unit 58 will be described.

First of all, the control flow of short circuit diagnosis control of a first example will be described with reference to FIG. 14 and FIG. 15. The short circuit diagnosis control of the first example is the case of using the open circuit voltage OCV as the voltage of the power supply 12.

First, the aerosol generation request detecting unit 51 detects the aerosol generation request based on the output result of the inhalation sensor 15 (STEP S11). By acquiring a short circuit state of the power supply 12 in response to a request for aerosol generation from a user, it is possible to make the user recognize the short circuit determination result. In the case where the aerosol generation request detecting unit 51 has detected the request for aerosol generation ("Yes" in STEP S11), the power-supply voltage acquiring unit 55 acquires the open circuit voltage OCV (STEP S12); whereas in the case where the aerosol generation request detecting unit 51 has not detected the request for aerosol generation ("No" in STEP S11), the process of STEP S11 is repeated.

After acquiring the open circuit voltage OCV in STEP S12, the power-supply voltage acquiring unit 55 acquires the previous open circuit voltage OCV (STEP S13). The previous open circuit voltage OCV can be acquired from the memory 18 retaining the previous open circuit voltage acquired in advance before the previous aerosol generation. Also, the order of STEP S12 and STEP S13 may be reversed. Subsequently, the threshold setting unit 57 sets a threshold TH (STEP S14). This threshold TH is set based on the amount of change of the voltage of the power supply 12 attributable to discharging performed after the acquisition of the previous open circuit voltage OCV, i.e. a voltage drop, and as described above, the threshold setting unit 57 may set or correct a threshold TH based on the voltage of the power supply 12, the state of deterioration of the power supply 12, and the like.

Subsequently, the short-circuit detection unit 58 compares the threshold TH set by the threshold setting unit 57 with the difference between the acquired previous open circuit voltage OCV and the acquired current open circuit voltage OCV, thereby determining whether the difference between the previous open circuit voltage OCV and the current open circuit voltage OCV is equal to or smaller than the threshold TH, or not (STEP S15). In the case where it is determined as the result that the difference between the previous open circuit voltage OCV and the current open circuit voltage OCV is equal to or smaller than the threshold TH ("Yes" in STEP S15), the short-circuit detection unit 58 determines that the power supply 12 is normal, i.e. a short circuit has not occurred (STEP S16), and the power control unit 53 performs PWM control for aerosol generation (STEP S17). Meanwhile, in the case where it is determined in STEP S15 that the difference between the previous open circuit voltage OCV and the current open circuit voltage OCV is larger than the threshold TH ("No" in STEP S15), the notification control unit 54 notifies the user that a short circuit has occurred (STEP S18).

The short-circuit detection unit 58 may detect whether a short circuit is an internal short circuit or an external short circuit, i.e. it may distinctively detect the type of a short circuit, in the case where a short circuit has occurred, in addition to whether a short circuit of the power supply 12 has occurred. In general, internal short circuits cause larger voltage drops as compared to external short circuits. In other words, the difference between the previous open circuit voltage OCV and the current open circuit voltage OCV during an internal short circuit is larger than the difference between the previous open circuit voltage OCV and the current open circuit voltage OCV during an external short circuit. Therefore, in STEP S15, the short-circuit detection unit 58 determines that the short circuit is an internal short circuit, in the case where the difference between the threshold TH and the difference between the previous open circuit voltage OCV and the current open circuit voltage OCV is large, and determines that the short circuit is an external short circuit, in the case where the difference between the threshold TH and the difference between the previous open circuit voltage OCV and the current open circuit voltage OCV is small.

Since the short-circuit detection unit 58 distinctively detects internal short circuits and external short circuits, the notification control unit 54 can notify the user that it is required to replace the power supply 12, if an internal short circuit occurs, and can notify the user that it is required to charge the power supply 12, if an external short circuit occurs. Therefore, it is possible to urge the user to take appropriate actions depending on short circuits.

Now, the control flow of short circuit diagnosis control of a second example will be described with reference to FIG. 16 and FIG. 17. The short circuit diagnosis control of the second example is the case of using the closed circuit voltage CCV as the voltage of the power supply 12. By the way, steps identical to those in the control flow of the short circuit diagnosis control of the first example will be described in brief or will not be described, and different steps will be described in detail.

First, the aerosol generation request detecting unit 51 detects the aerosol generation request based on the output result of the inhalation sensor 15 (STEP S11). In the case where the aerosol generation request detecting unit 51 has detected the request for aerosol generation ("Yes" in STEP S11), the power-supply voltage acquiring unit 55 acquires the closed circuit voltage CCV (STEP S22); whereas in the case where the aerosol generation request detecting unit 51 has not detected the request for aerosol generation ("No" in STEP S11), the process of STEP S11 is repeated.

After acquiring the closed circuit voltage CCV in STEP S12, the power-supply voltage acquiring unit 55 acquires the previous closed circuit voltage CCV (STEP S23). The closed circuit voltage CCV can be acquired from the memory 18 retaining the previous closed circuit voltage acquired in advance before the previous aerosol generation or immediately after the start of the previous aerosol generation. In the case of using the closed circuit voltage CCV in the short circuit diagnosis control, as described above, as for the pre-discharging voltage and the post-discharging voltage, it is required to match the timings to acquire them after a predetermined period including 0 passes from when the closing instruction is sent to the switch 19. Subsequently, the threshold setting unit 57 sets a threshold TH (STEP S24). This threshold TH is set based on the amount of change of the voltage of the power supply 12 attributable to discharging performed after the acquisition of the previous closed circuit voltage CCV, i.e. a voltage drop, and as described above, the threshold setting unit 57 may set or correct a threshold TH based on the voltage of the power supply 12, the state of deterioration of the power supply 12, and the like.

Subsequently, the short-circuit detection unit 58 compares the threshold TH set by the threshold setting unit 57 with the difference between the acquired previous closed circuit voltage CCV and the acquired current closed circuit voltage CCV, thereby determining whether the difference between the previous closed circuit voltage CCV and the current closed circuit voltage CCV is equal to or smaller than the threshold TH, or not (STEP S25). In the case where it is determined as the result that the difference between the previous closed circuit voltage CCV and the current closed circuit voltage CCV is equal to or smaller than the threshold TH ("Yes" in STEP S25), the short-circuit detection unit 58 determines that the power supply 12 is normal, i.e. a short circuit has not occurred (STEP S16), and the power control unit 53 performs PWM control for aerosol generation (STEP S17). Meanwhile, in the case where it is determined in STEP S25 that the difference between the previous closed circuit voltage CCV and the current closed circuit voltage CCV is larger than the threshold TH ("No" in STEP S25), the notification control unit 54 notifies the user that a short circuit has occurred (STEP S18).

By the way, in STEP S13 of the short circuit diagnosis control of the first example and STEP S23 of the short circuit diagnosis control of the second example, when the power-supply voltage acquiring unit 55 acquires the previous open circuit voltage OCV, if the interval between before the discharging and after the discharging exceeds a predetermined time, control may be performed such that detection on a short circuit of the power supply 12 is not performed. The interval between before the discharging and after the discharging may be measured by a timer. Also, programming may be performed such that after the predetermined time passes, the previous open circuit voltage is automatically deleted from the memory 18. In this case, if the interval between before the discharging and after the discharging becomes a long time, detection on a short circuit of the power supply 12 is not performed. Therefore, it is possible to prevent erroneous detection of a short circuit attributable to natural discharge or the like.

Figure 14:
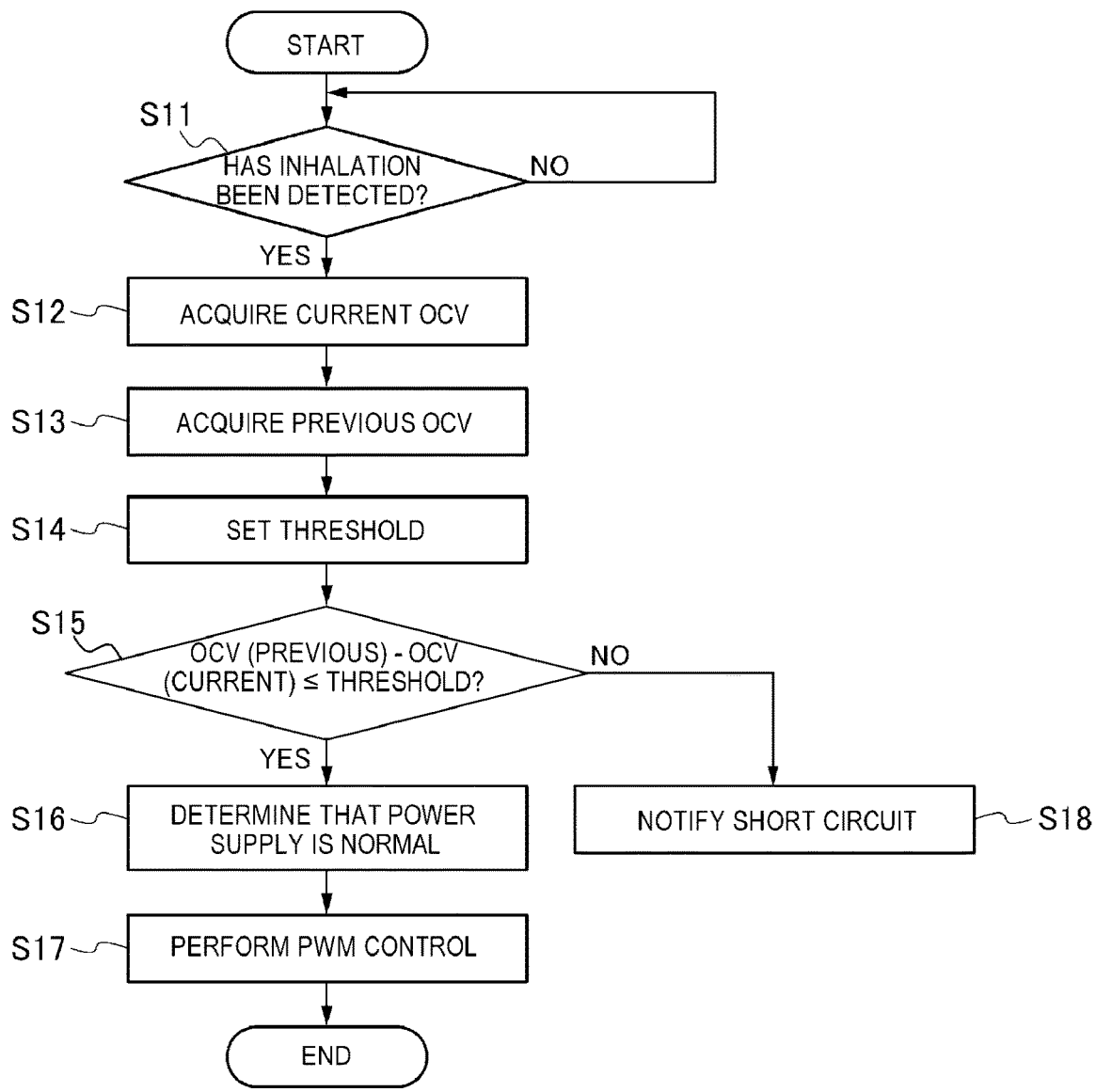
FIG. 14 is the flow chart of the control flow of short circuit diagnosis control of the first example.
Figure 15:
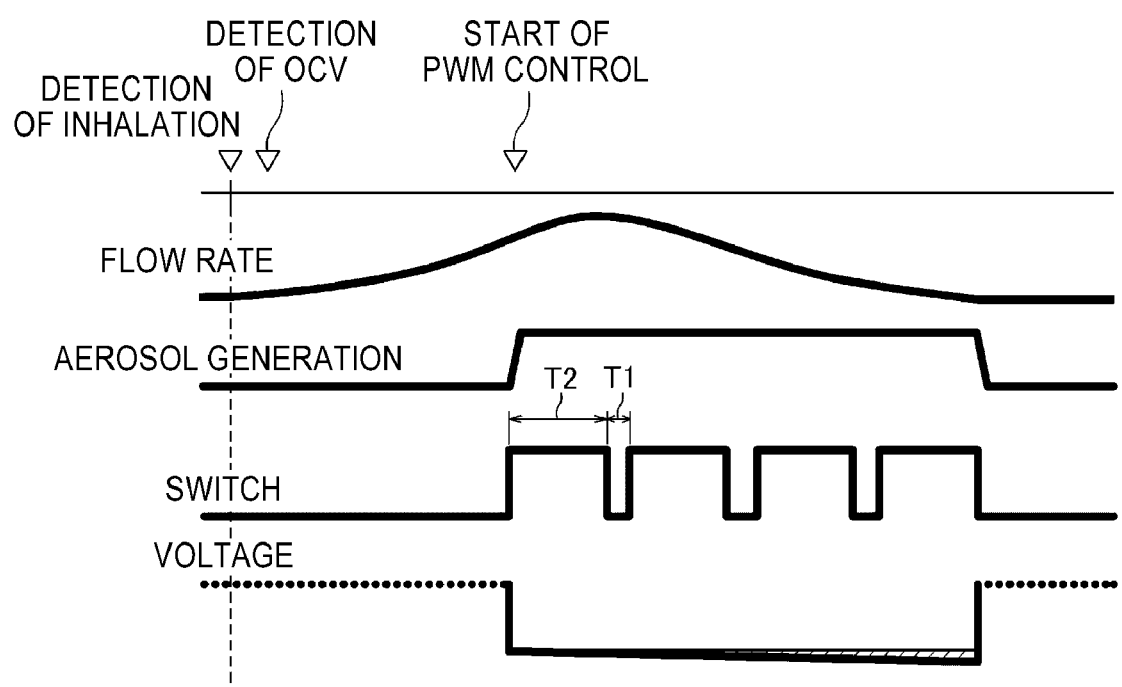
FIG. 15 is the timing chart of the short circuit diagnosis control of FIG. 14.
Figure 16:
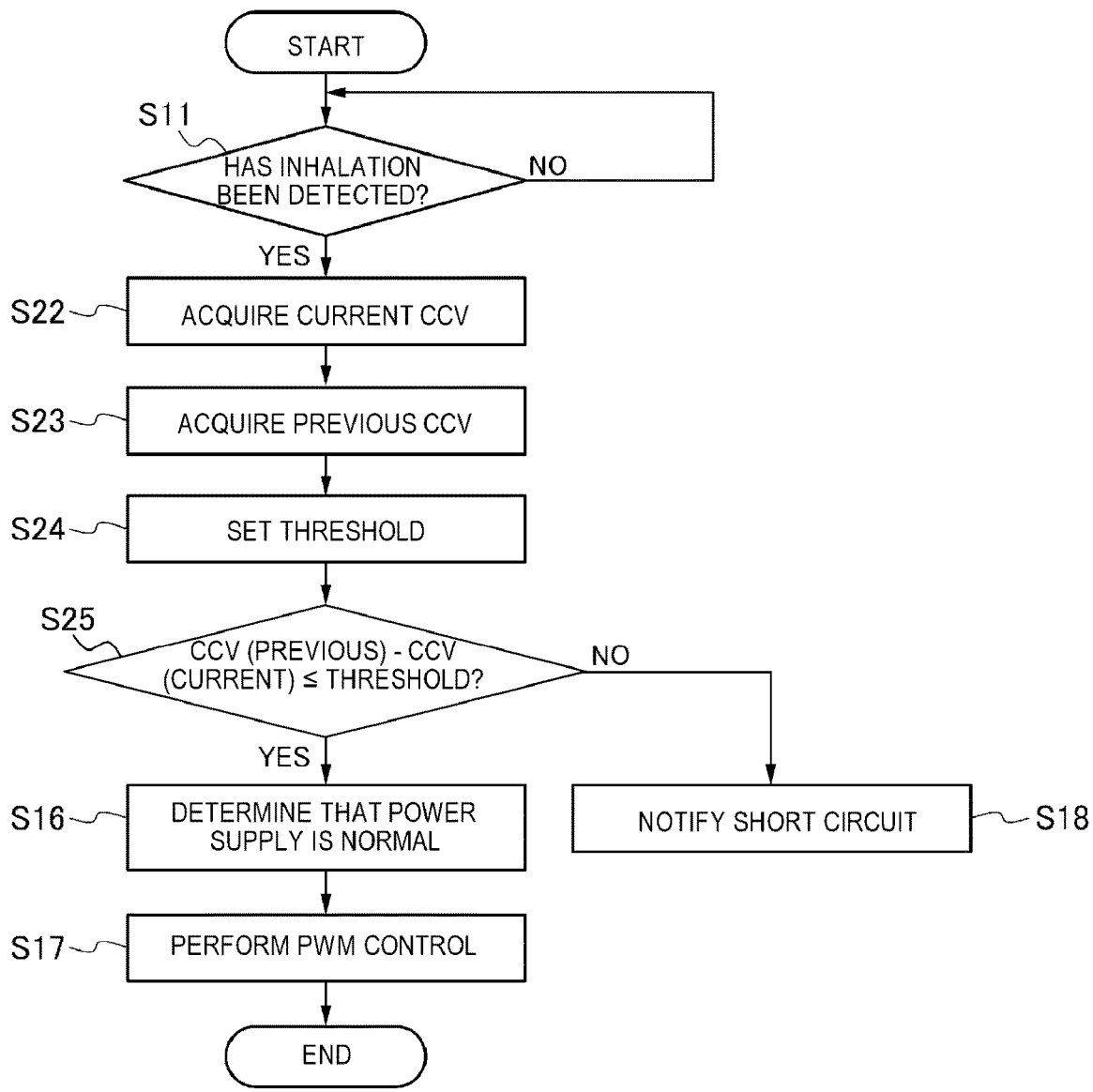
FIG. 16 is the flow chart of the control flow of short circuit diagnosis control of the second example.
Figure 17:
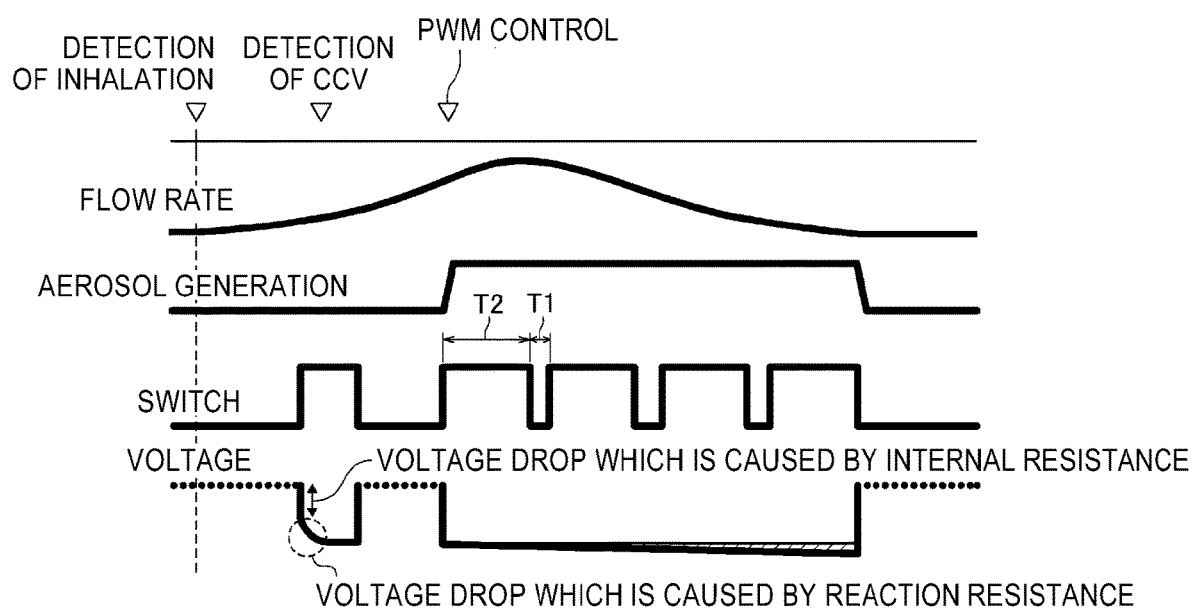
FIG. 17 is the timing chart of the short circuit diagnosis control of FIG. 16.

By the way, in the short circuit diagnosis process of the first example shown in FIG. 14 and the short circuit diagnosis process of the second example shown in FIG. 16, the previous open circuit voltage OCV or the previous closed circuit voltage CCV is acquired after the aerosol generation request is detected, not after the previous aerosol generation. Immediately after aerosol generation, since the temperature of the power supply 12 rises due to discharging, the current open circuit voltage OCV or the current closed circuit voltage CCV may be influenced. Meanwhile, in the timing when the aerosol generation request is detected, the temperature of the power supply 12 is likely to be around the room temperature. Therefore, like in the short circuit diagnosis process of the first example or the short circuit diagnosis process of the second example, by making the conditions for acquiring the voltage as similar as possible, it is possible to improve the accuracy of the short circuit diagnosis process.

However, the present invention is not limited to the above-described embodiment, and modifications, improvements, etc. can be made properly.

In this specification, at least the following inventions (1) to (20) are disclosed. Moreover, although the corresponding constituent elements and the like in the embodiments described above are shown in parentheses, it is not limited thereto.

(1) A power supply unit (the power supply unit 10) for an aerosol inhaler (the aerosol inhaler 1), the power supply unit comprising:
  a power supply (the power supply 12) able to discharge power to a load (the load 21) for generating an aerosol from an aerosol source (the aerosol source 22);
  a control unit (the control unit 50) configured to control the power supply; and
  a sensor (the voltage sensor 16) configured to output a value related to a remaining amount of the power supply, wherein
  the control unit detects a short circuit of the power supply based on an output value of the sensor.

According to (1), the control unit detects a short circuit of the power supply based on the output value (voltage) of the sensor. Therefore, it is possible to determine whether the power supply is normal or not. However, the output value of the sensor is not limited to the voltage of the power supply, and needs only to be a value (voltage-related value) from which it is possible to derive the voltage of the power supply.

(2) The power supply unit according to (1), wherein
the control unit detects the short circuit, based on a first output value (the pre-discharging voltage) which is an output value of the sensor obtained before discharging, and a second output value (the post-discharging voltage) which is an output value of the sensor obtained after the discharging.

According to (2), the short circuit is detected based on the first output value and the second output value obtained before and after the discharging. Therefore, it is possible to perform short circuit detection at an appropriate timing, i.e. after a load is applied to the power supply.

(3) The power supply unit according to (2), wherein
the discharging is discharging to another load different from the load.

According to (3), the short circuit is detected based on the first output value and the second output value obtained before and after discharging to another load less than to discharging to the load for generating an aerosol. Therefore, it is possible to suppress damage to the power supply during occurrence of a short circuit.

(4) The power supply unit according to (3), wherein
the discharging is discharging to the load.

According to (4), the short circuit is detected based on the first output value and the second output value obtained before and after discharging to the load. Therefore, it is possible to perform short circuit detection at an appropriate timing, i.e. after discharging when the largest load is applied to the power supply.

(5) The power supply unit according to any one of (2) to (4), wherein
the control unit detects the short circuit in a case where a difference between the first output value and the second output value is larger than a threshold (the threshold TH) which is an amount of change of the value related to the remaining amount of the power supply and attributable to the discharging.

According to (5), if a short circuit has not occurred in the power supply, the difference between the first output value and the second output value becomes equal to or smaller than a threshold which is set based on the amount of change of the value related to the remaining amount of the power supply and attributable to discharging. However, in the case where a short circuit has occurred in the power supply, since the difference between the first output value and the second output value becomes large, the difference between the first output value and the second output value becomes larger than the threshold. Therefore, it is possible to detect the short circuit of the power supply.

(6) The power supply unit according to (2) or (4), wherein
the power supply unit includes at least a part of a circuit configured to electrically connect the power supply and the load, and
during the discharging, the control unit controls the circuit such that power per unit time which is supplied to the load is constant or variation in power per unit time which is supplied to the load is suppressed, and
in a case where a difference between the first output value and the second output value is larger than a threshold which is an amount of change of the value related to the remaining amount of the power supply and is set or corrected based on time for which the discharging has been performed, the control unit detects the short circuit.

According to (6), in the case of performing constant power control during discharging, a threshold is set or corrected based on the time for which the discharging has been performed. Therefore, it is possible to set an appropriate threshold without requiring complicated calculation.

(7) The power supply unit according to (2) or (4), wherein
the power supply unit includes at least a part of a circuit configured to electrically connect the power supply and the load, and
during the discharging, the control unit controls the circuit such that power per unit time which is supplied to the load is constant or variation in power per unit time which is supplied to the load is suppressed, and controls the circuit such that time for which the discharging is performed does not exceed a predetermined time (the maximum power supply time), and
in a case where a difference between the first output value and the second output value is larger than a threshold which is an amount of change of the value related to the remaining amount of the power supply in a case where the discharging has been performed for the predetermined time, the control unit detects the short circuit.

According to (7), in the case of performing constant power control such that the time for which discharging is performed does not exceed the predetermined time, a threshold is set on the assumption that constant power has been discharged only for the predetermined time. Therefore, it is possible to set an appropriate threshold without requiring complicated calculation.

(8) The power supply unit according to (2) or (4), wherein
the power supply unit includes at least a part of a circuit configured to electrically connect the power supply and the load, and
during the discharging, the control unit controls the circuit such that time for which the discharging is performed does not exceed a predetermined time (the maximum power supply time), and
in a case where a difference between the first output value and the second output value is larger than a threshold which is an amount of change of the value related to the remaining amount of the power supply in a case where maximum power which can be supplied to the load has been supplied only for the predetermined time, the control unit detects the short circuit.

According to (8), in the case of performing control such that the time for which discharging is performed does not exceed the predetermined time, a threshold is set on the assumption that the maximum power which can be supplied to the load has been discharged only for the predetermined time. Therefore, it is possible to set an appropriate threshold without requiring complicated calculation.

(9) The power supply unit according to any one of (5) to (8), wherein
the value related to the remaining amount is a voltage of the power supply, and
the threshold is set based on a degree of change of the voltage of the power supply in a case where the voltage of the power supply belongs to a non-plateau region (the non-plateau region P1 or P3) of a region which is defined by a full charging voltage and a discharge cutoff voltage.

According to (9), the threshold is set based on the degree of change of the voltage of the power supply in the case where the voltage of the power supply belongs to a non-plateau region of the region which is defined by the full charging voltage and the discharge cutoff voltage. Therefore, it is possible to suppress erroneous detection of a short circuit attributable to a difference in the voltage of the power supply.

(10) The power supply unit according to any one of (5) to (8), wherein the value related to the remaining amount is a voltage of the power supply, and the threshold is set based on a degree of change of the voltage of the power supply in a case where the voltage of the power supply belongs to a region (the non-plateau region P1) in which an amount of change of the voltage of the power supply per unit discharge amount is largest, of a region which is defined by a full charging voltage and a discharge cutoff voltage.

According to (10), the threshold is set based on the degree of change of the voltage of the power supply in the case where the voltage of the power supply belongs to a region in which the amount of change of the voltage of the power supply per unit discharge amount is largest, of the region which is defined by the full charging voltage and the discharge cutoff voltage. Therefore, it is possible to suppress erroneous detection of a short circuit attributable to a difference in the voltage of the power supply.

(11) The power supply unit according to any one of (5) to (10), wherein the control unit is configured to set or correct the threshold based on a state of deterioration of the power supply or a voltage of the power supply.

According to (11), the threshold is set or corrected based on the state of deterioration of the power supply or the voltage of the power supply. Therefore, it is possible to set an optimal threshold according to the state of the power supply, and the accuracy of short circuit detection improves.

(12) The power supply unit according to any one of (2) to (11), wherein the value related to the remaining amount of the power supply is a voltage of the power supply, and the first output value and the second output value are open circuit voltages of the power supply.

According to (12), the short circuit is detected based on the first output value and the second output value which are open circuit voltages. Therefore, the accuracy of short circuit detection improves as compared to the case of detecting a short circuit based on an open circuit voltage and a closed circuit voltage.

(13) The power supply unit according to any one of (2) to (11), wherein the value related to the remaining amount of the power supply is a voltage of the power supply, and the first output value and the second output value are closed circuit voltages of the power supply.

According to (13), the short circuit is detected based on the first output value and the second output value which are closed circuit voltages. Therefore, the accuracy of short circuit detection improves as compared to the case of detecting a short circuit based on an open circuit voltage and a closed circuit voltage.

(14) The power supply unit according to (13), further comprising:

a switch (the switch 19) configured to allow or shut off supply of power from the power supply, wherein the first output value and the second output value are closed circuit voltages of the power supply which are obtained after a predetermined period including 0 passes from when the control unit sends a closing instruction to the switch.

According to (14), the acquisition timings of the first output value and the second output value which are closed circuit voltages are matched. Therefore, the accuracy of short circuit detection further improves.

(15) The power supply unit according to (14), wherein the predetermined period is set based on a time constant (the mitigation time) in a case where change of a closed circuit voltage of the power supply is considered in a primary delay system.

According to (15), the short circuit is detected based on the first output value and the second output value which are closed circuit voltages which are obtained after the predetermined period set based on the time constant passes. Therefore, the accuracy of short circuit detection improves.

(16) The power supply unit according to any one of (2) to (15), wherein the control unit distinctively detects an internal short circuit of the power supply and an external short circuit of the power supply, based on a difference between the first output value and the second output value.

According to (16), the internal short circuit of the power supply and the external short circuit of the power supply are distinctively detected. Therefore, it is possible to perform an appropriate notification or procedure according to the location where a short circuit has occurred.

(17) The power supply unit according to (16), wherein the difference between the first output value and the second output value for detecting the internal short circuit are larger than the difference between the first output value and the second output value for detecting the external short circuit.

According to (17), the internal short circuit of the power supply and the external short circuit of the power supply are distinguished according to the difference between the first output value and the second output value. Therefore, it is possible to determine the type of a short circuit with high accuracy.

(18) The power supply unit according to any one of (2) to (17), wherein the control unit does not detect the short circuit of the power supply in a case where an interval between before the discharging and after the discharging exceeds a predetermined period.

According to (18), detection on a short circuit of the power supply is not performed in the case where the interval between before the discharging and after the discharging exceeds the predetermined period. Therefore, it is possible to prevent erroneous detection of a short circuit attributable to natural discharge or the like.

(19) A control method of a power supply unit for an aerosol inhaler, the power supply unit including a power supply able to discharge power to a load for generating an aerosol from an aerosol source, the control method comprising:

detecting a short circuit of the power supply based on a value related to a remaining amount of the power supply.

According to (19), a short circuit of the power supply is detected based on a value related to the remaining amount of the power supply. Therefore, it is possible to determine whether the power supply is normal or not.

(20) A control program of a power supply unit for an aerosol inhaler, the power supply unit including a power supply able to discharge power to a load for generating an aerosol from an aerosol source, the control program comprising:

detecting a short circuit of the power supply based on a value related to a remaining amount of the power supply.

According to (20), a short circuit of the power supply is detected based on a value related to the remaining amount of the power supply. Therefore, it is possible to determine whether the power supply is normal or not.

According to (1), (19), and (20), a short circuit of the power supply is detected based on the output value (voltage) of an output sensor. Therefore, it is possible to determine whether the power supply is normal or not. Therefore, it is possible to urge the user and so on to replace the power supply at an appropriate timing. Therefore, there is energy saving effect in which it is possible to maximize the period for which it is possible to use the power supply without replacing with a new one.

What is claimed is:

1. A power supply unit for an aerosol inhaler, the power supply unit comprising:
   a power supply configured to discharge power to a load for generating an aerosol from an aerosol source;
   a sensor configured to output a value related to a remaining amount of the power supply; and
   circuitry configured to
     determine that a request for aerosol generation has been received;
     detect, in response to determining that the request for aerosol has been received and before generating the aerosol, whether there is a short circuit of the power supply based on a relationship between a first output value and a second output value, wherein the first output value is an output value of the sensor obtained prior to discharging, and the second output value is an output value of the sensor obtained after the discharging; and
     perform control to discharge power from the power supply to the load to generate the aerosol only when no short circuit of the power supply is detected, wherein
   in a case that the short circuit is detected, the circuitry is configured to
     detect that the type of short circuit is an internal short circuit in a case that a difference between the first output value and the second output value is greater than a threshold; and
     detect that the type of short circuit is an external short circuit in a case that the difference between the first output value and the second output value is less than the threshold.

2. The power supply unit of claim 1, wherein
the discharging is discharging to another load different from the load for generating the aerosol from the aerosol source.

3. The power supply unit of claim 1, wherein
the discharging is discharging for aerosol generation to the load.

4. The power supply unit of claim 1, wherein
the threshold corresponds to an amount of change of the value related to the remaining amount of the power supply and attributable to the discharging.

5. The power supply unit of claim 1, wherein
the value related to the remaining amount of the power supply is a voltage of the power supply, and
the first output value and the second output value are open circuit voltages of the power supply.

6. The power supply unit of claim 1, wherein
the value related to the remaining amount of the power supply is a voltage of the power supply, and
the first output value and the second output value are closed circuit voltages of the power supply.

7. The power supply unit of claim 1, further comprising:
a connection interface, wherein
the power supply unit is configured to be detachably connected to the load via the connection interface.

8. The power supply unit of claim 1, further comprising:
a charger configured to charge the power supply in a case that external power is supplied to the power supply unit.

9. The power supply unit of claim 4, wherein
the remaining amount of power of the power supply corresponds to a voltage value of the power supply detected by the sensor, and
the threshold is set based on a difference between a theoretical drop in a detected voltage of the power supply before and after discharging in a case that power supply is fully charged.

10. The power supply unit of claim 4, wherein
the remaining amount of power of the power supply corresponds to a voltage value of the power supply detected by the sensor, and
the circuitry is configured to dynamically modify the threshold based on a detected deterioration state of the battery.

11. The power supply unit of claim 4, wherein the circuitry is configured to:
estimate a state of health of the power supply based on a cumulative discharge amount of the power supply; and
set the threshold based on the estimated state of the health of the power supply.

12. The power supply unit of claim 11, further comprising:
a memory configured to store a correspondence between a plurality of estimated states of health of the power supply and a plurality of threshold settings corresponding to each estimated state of health, wherein
the circuity is configured to access the memory to set the threshold based on the estimate health of the power supply.

13. The power supply unit of claim 1, further comprising:
a light emitting diode (LED), wherein
the circuitry is configured to control the LED to output a notification and perform control to not discharge power from the power supply to the load to generate the aerosol when a short circuit of the power supply is detected.

14. A power supply unit for an aerosol inhaler, the power supply unit comprising:
a power supply configured to discharge power to a load for generating an aerosol from an aerosol source;
a connection interface, wherein the power supply unit is configured to be detachably connected to the load via the connection interface;
a sensor configured to output a value related to a remaining amount of the power supply; and
control circuitry configured to
  control the power supply;
  determine that a request for aerosol generation has been received;
  detect, in response to determining that the request for aerosol has been received and before generating the aerosol, whether there is a short circuit of the power supply, based on a first output value which is an output value of the sensor obtained before discharging for aerosol generation, and a second output value which is an output value of the sensor obtained after the discharging; and perform control to discharge power from the power supply to the load to generate the aerosol only when no short circuit of the power supply is detected, wherein in a case that the short circuit is detected, the circuitry is configured to detect that the type of short circuit is an internal short circuit in a case that a difference between the first output value and the second output value is greater than a threshold; and detect that the type of short circuit is an external short circuit in a case that the difference between the first output value and the second output value is less than the threshold.

15. The power supply unit of claim 14, wherein the power supply unit includes at least a part of a circuit configured to electrically connect the power supply and the load, and during the discharging, the control circuitry controls the circuit such that power per unit time which is supplied to the load is constant or variation in power per unit time which is supplied to the load is suppressed, and the threshold corresponds to an amount of change of the value related to the remaining amount of the power supply and is set or corrected based on time for which the discharging has been performed.

16. The power supply unit of claim 14, wherein the power supply unit includes at least a part of a circuit configured to electrically connect the power supply and the load, and during the discharging, the control circuitry controls the circuit such that power per unit time which is supplied to the load is constant or variation in power per unit time which is supplied to the load is suppressed, and controls the circuit such that time for which the discharging is performed does not exceed a predetermined time, and the threshold corresponds to an amount of change of the value related to the remaining amount of the power supply in a case where the discharging has been performed for the predetermined time.

17. The power supply unit of claim 14, wherein the power supply unit includes at least a part of a circuit configured to electrically connect the power supply and the load, and during the discharging, the control circuitry controls the circuit such that time for which the discharging is performed does not exceed a predetermined time, and the threshold corresponds to an amount of change of the value related to the remaining amount of the power supply in a case where maximum power which can be supplied to the load has been supplied only for the predetermined time.

18. The power supply unit of claim 14, further comprising:

a charger configured to charge the power supply in a case that external power is supplied to the power supply unit.

19. A power supply unit for an aerosol inhaler, the power supply unit comprising:

a power supply able to discharge power to a load for generating an aerosol from an aerosol source;

a switch configured to allow or shut off supply of power from the power supply;

circuitry configured to control the power supply; and a sensor configured to output a voltage of the power supply, wherein the circuitry determines that a request for aerosol generation has been received;

detects, in response to determining that the request for aerosol has been received and before generating the aerosol, whether there is a short circuit of the power supply, based on a first output value which is an output value of the sensor obtained before discharging, and a second output value which is an output value of the sensor obtained after the discharging, and the first output value and the second output value are closed circuit voltages of the power supply which are obtained after a predetermined period including 0 passes from when the circuitry sends a closing instruction to the switch, wherein in a case that the short circuit is detected, the circuitry distinctively detects a type of the short circuit based on the relationship between the first output value and the second output value, and performs control to discharge power from the power supply to the load to generate the aerosol only when no short circuit of the power supply is detected, wherein the circuitry is configured to detect that the type of short circuit is an internal short circuit in a case that a difference between the first output value and the second output value is greater than a threshold; and detect that the type of short circuit is an external short circuit in a case that the difference between the first output value and the second output value is less than the threshold.

20. The power supply unit of claim 19, wherein the predetermined period is set based on a time constant in a case where change of a closed circuit voltage of the power supply is considered in a primary delay system.

* * * * *